United States Patent
Aljumah et al.

(10) Patent No.: US 11,845,705 B2
(45) Date of Patent: Dec. 19, 2023

(54) PROCESSES INTEGRATING HYDROCARBON CRACKING WITH METATHESIS FOR PRODUCING PROPENE

(71) Applicant: Saudi Arabian Oil Company, Dhahran (SA)

(72) Inventors: Furqan Aljumah, Dhahran (SA); Sohel Shaikh, Dhahran (SA); Zhonglin Zhang, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/404,379

(22) Filed: Aug. 17, 2021

(65) Prior Publication Data

US 2023/0093607 A1    Mar. 23, 2023

(51) Int. Cl.
*C07C 4/06* (2006.01)
*C07C 5/13* (2006.01)
(Continued)

(52) U.S. Cl.
CPC .............. *C07C 4/06* (2013.01); *B01J 19/0013* (2013.01); *C07C 4/08* (2013.01); *C07C 5/13* (2013.01);
(Continued)

(58) Field of Classification Search
None
See application file for complete search history.

(56) References Cited

U.S. PATENT DOCUMENTS

| 3,442,821 A | 5/1969 | Hilfman |
| 3,546,313 A | 12/1970 | Banks |

(Continued)

FOREIGN PATENT DOCUMENTS

| CN | 100448820 C | 1/2009 |
| CN | 101514135 A | 8/2009 |

(Continued)

OTHER PUBLICATIONS

U.S. Notice of Allowance and Fee(s) Due dated Feb. 25, 2022 pertaining to U.S. Appl. No. 16/775,677, filed Jan. 29, 2020, 14 pages.

(Continued)

*Primary Examiner* — Youngsul Jeong
*Assistant Examiner* — Alyssa L Cepluch
(74) *Attorney, Agent, or Firm* — DINSMORE & SHOHL LLP

(57) ABSTRACT

Processes for producing olefins include passing a hydrocarbon feed to a hydrocarbon cracking unit that cracks the hydrocarbon feed to produce a cracker effluent, passing the cracker effluent to a cracker effluent separation system that separates the cracker effluent to produce at least a cracking C4 effluent including 1-butene, 1,3-butadiene, and isobutene, passing the cracking C4 effluent to an SHIU that contacts the cracking C4 effluent with hydrogen in the presence of a selective hydrogenation catalyst to produce a hydrogenation effluent having a 2-butenes concentration greater than or equal to the sum of the concentrations of 1-butene and isobutene. The processes include passing the hydrogenation effluent to a metathesis unit that contacts the hydrogenation effluent with a metathesis catalyst and a cracking catalyst downstream of the metathesis catalyst to produce a metathesis reaction effluent comprising at least propene.

16 Claims, 7 Drawing Sheets

(51) Int. Cl.
*C07C 6/04* (2006.01)
*B01J 19/00* (2006.01)
*C07C 4/08* (2006.01)

(52) U.S. Cl.
CPC ....... *C07C 6/04* (2013.01); *B01J 2219/00051* (2013.01); *B01J 2219/00162* (2013.01); *B01J 2219/00189* (2013.01)

(56) References Cited

U.S. PATENT DOCUMENTS

| | | | |
|---|---|---|---|
| 3,586,731 | A | 6/1971 | Deckelsberg |
| 3,621,073 | A * | 11/1971 | McGrath ............... C07C 5/2556 585/324 |
| 3,702,886 | A | 11/1972 | Argauer et al. |
| 3,728,415 | A | 4/1973 | Arganbright |
| 4,024,201 | A | 5/1977 | Takahashi |
| 4,071,471 | A | 1/1978 | Banks et al. |
| 4,575,575 | A | 3/1986 | Drake et al. |
| 4,609,769 | A | 9/1986 | Kukes et al. |
| 5,026,935 | A | 6/1991 | Leyshon et al. |
| 5,026,936 | A | 6/1991 | Leyshon et al. |
| 5,191,131 | A | 3/1993 | Takahata et al. |
| 5,439,859 | A | 8/1995 | Durante et al. |
| 5,523,502 | A | 6/1996 | Rubin |
| 5,674,955 | A * | 10/1997 | Kerr ...................... C08F 210/08 526/221 |
| 5,877,365 | A | 3/1999 | Chodorge et al. |
| 6,159,433 | A | 12/2000 | Chodorge et al. |
| 6,207,115 | B1 | 3/2001 | Chodorge et al. |
| 6,210,562 | B1 | 4/2001 | Xie et al. |
| 6,242,661 | B1 * | 6/2001 | Podrebarac ............. C07C 7/148 208/138 |
| 6,538,168 | B1 | 3/2003 | Schwab et al. |
| 6,580,009 | B2 | 6/2003 | Schwab et al. |
| 6,586,649 | B1 | 7/2003 | Botha et al. |
| 6,646,172 | B1 | 11/2003 | Schwab et al. |
| 6,777,582 | B2 | 8/2004 | Gartside et al. |
| 6,977,321 | B1 | 12/2005 | Dath et al. |
| 7,214,841 | B2 | 5/2007 | Gartside et al. |
| 7,754,647 | B2 | 7/2010 | Schubert et al. |
| 7,754,934 | B2 | 7/2010 | Tsunoda et al. |
| 7,816,572 | B2 * | 10/2010 | Leyshon ................. C07C 11/18 585/656 |
| 7,977,522 | B2 | 7/2011 | Takai et al. |
| 8,299,313 | B2 | 10/2012 | Takai et al. |
| 8,324,440 | B2 | 12/2012 | Popp et al. |
| 8,362,308 | B2 | 1/2013 | Stephan et al. |
| 8,440,874 | B2 | 5/2013 | Ramachandran et al. |
| 8,586,813 | B2 | 11/2013 | Ramachandran et al. |
| 8,722,568 | B2 | 5/2014 | Popp et al. |
| 9,834,497 | B2 | 12/2017 | Shaikh et al. |
| 9,884,794 | B2 | 2/2018 | Al-Khattaf et al. |
| 10,005,703 | B2 | 6/2018 | Abudawoud et al. |
| 10,052,618 | B2 | 8/2018 | Al-Khattaf et al. |
| 10,059,645 | B2 | 8/2018 | Shaikh et al. |
| 10,065,906 | B2 | 9/2018 | Shaikh et al. |
| 10,214,466 | B2 | 2/2019 | Shaikh et al. |
| 10,329,225 | B2 | 6/2019 | Khokhar et al. |
| 10,532,347 | B2 | 1/2020 | Al-Khattaf et al. |
| 10,550,048 | B2 | 2/2020 | Alshafei et al. |
| 10,583,423 | B2 | 3/2020 | Al-Khattaf et al. |
| 10,919,822 | B2 | 2/2021 | Khokhar et al. |
| 10,934,231 | B2 | 3/2021 | Alshafei et al. |
| 10,961,171 | B2 | 3/2021 | Khokhar et al. |
| 2003/0176754 | A1 | 9/2003 | Gartside et al. |
| 2004/0254411 | A1 | 12/2004 | Steinbrenner et al. |
| 2005/0014981 | A1 | 1/2005 | Gartside et al. |
| 2005/0124839 | A1 | 6/2005 | Gartside et al. |
| 2006/0047176 | A1 | 3/2006 | Gartside et al. |
| 2006/0293548 | A1 | 12/2006 | Spamer et al. |
| 2007/0038010 | A1 | 2/2007 | Xie et al. |
| 2007/0225478 | A1 | 9/2007 | Querci et al. |
| 2008/0033223 | A1 | 2/2008 | Sigl et al. |
| 2008/0171655 | A1 | 7/2008 | Creyghton et al. |
| 2010/0041930 | A1 | 2/2010 | Gartside et al. |
| 2010/0168487 | A1 | 7/2010 | Sawyer et al. |
| 2010/0234542 | A1 | 9/2010 | Blackborow et al. |
| 2011/0021858 | A1 | 1/2011 | Ramachandran et al. |
| 2011/0152595 | A1 | 6/2011 | Takai et al. |
| 2011/0196185 | A1 | 8/2011 | Krawczyk et al. |
| 2012/0108864 | A1 | 5/2012 | Gartside et al. |
| 2012/0283090 | A1 | 11/2012 | Popp et al. |
| 2012/0289617 | A1 | 11/2012 | Wang et al. |
| 2013/0085311 | A1 | 4/2013 | Youn et al. |
| 2013/0165701 | A1 | 6/2013 | Zhou et al. |
| 2013/0245348 | A1 | 9/2013 | Vermeiren et al. |
| 2013/0303806 | A1 | 11/2013 | Winterberg et al. |
| 2014/0148629 | A1 | 5/2014 | Van Hal et al. |
| 2015/0141720 | A1 | 5/2015 | Ramachandran et al. |
| 2015/0141721 | A1 | 5/2015 | Choi et al. |
| 2015/0251968 | A1 | 9/2015 | Brianti et al. |
| 2016/0130197 | A1 | 5/2016 | Al-Khattaf et al. |
| 2016/0237006 | A1 | 8/2016 | Stoyanova et al. |
| 2016/0264990 | A1 | 9/2016 | Mankin et al. |
| 2017/0001925 | A1 | 1/2017 | Abudawoud et al. |
| 2017/0001926 | A1 | 1/2017 | Shaikh et al. |
| 2017/0001927 | A1 | 1/2017 | Al-Khattaf et al. |
| 2017/0001928 | A1 | 1/2017 | Shaikh et al. |
| 2017/0253540 | A1 | 9/2017 | Hfel et al. |
| 2018/0057425 | A1 | 3/2018 | Shaikh et al. |
| 2018/0142167 | A1 | 5/2018 | Al-Ghamdi et al. |
| 2018/0155642 | A1 * | 6/2018 | Al-Ghamdi ............ C10G 69/08 |
| 2018/0208524 | A1 | 7/2018 | Alshafei et al. |
| 2018/0208526 | A1 | 7/2018 | Alshafei et al. |
| 2018/0208527 | A1 | 7/2018 | Khokhar et al. |
| 2018/0230071 | A1 | 8/2018 | Bonduelle et al. |
| 2018/0346827 | A1 * | 12/2018 | Al-Ghamdi ................ B01J 8/26 |
| 2019/0367432 | A1 | 12/2019 | Al-Majnouni et al. |

FOREIGN PATENT DOCUMENTS

| | | | | |
|---|---|---|---|---|
| CN | 101531558 | A | 9/2009 | |
| CN | 102177223 | A | 9/2011 | |
| CN | 102325742 | A | 1/2012 | |
| CN | 104370676 | A | 2/2015 | |
| DE | 10013253 | A1 | 9/2001 | |
| EP | 304515 | B1 | 12/1991 | |
| EP | 838449 | A1 | 4/1998 | |
| EP | 920911 | A1 | 6/1999 | |
| EP | 2151424 | A1 | 2/2010 | |
| GB | 1110826 | * | 4/1968 | ............ B44C 7/022 |
| GB | 1205677 | A | 9/1970 | |
| JP | 2003500190 | A | 1/2003 | |
| JP | 2012500304 | A | 1/2012 | |
| KR | 1020210027788 | A | 3/2021 | |
| NL | 8403050 | A | 5/1986 | |
| RU | 2370314 | C1 | 10/2009 | |
| WO | 9929805 | A1 | 6/1999 | |
| WO | 0071255 | | 11/2000 | |
| WO | 2006089957 | A1 | 8/2006 | |
| WO | 2008136280 | A1 | 11/2008 | |
| WO | 2009015118 | A2 | 1/2009 | |
| WO | 2009117128 | A1 | 9/2009 | |
| WO | 2010019595 | A2 | 2/2010 | |
| WO | 2011136983 | A1 | 11/2011 | |
| WO | 2015055594 | A1 | 4/2015 | |
| WO | 2017003812 | A1 | 1/2017 | |
| WO | 2017003817 | A1 | 1/2017 | |
| WO | 2017003821 | A1 | 1/2017 | |
| WO | 2018088815 | A1 | 5/2018 | |

OTHER PUBLICATIONS

Chinese Office Action dated Mar. 24, 2022 pertaining to Chinese Patent Application No. 201880006954.X filed Jan. 18, 2018, 14 pages.

Arudra et al., "Silicalite-1 as Efficient Catalyst for Production of Propene from 1-Butene", ACS Catalysis, 2014, 4205-4212, 4, American Chemical Society.

Bortnovsky et al., "Cracking of pentenes to C2-C4 light olefins over zeolites and zeotypes Role of topology and acid site strength and

(56) References Cited

OTHER PUBLICATIONS concentration", Applied Catalysis A: General 287, pp. 203-213, 2005.
Balcar, et al., "Mesoporous molecular sieves as advanced supports for olefin metathesis catalysts", Coordination Chemistry Reviews 257, 2013, pp. 3107-3124, Czech Republic.
Barrett et al., "The Determination of Pore Volume and Area Distributions in Porous Substances. I. Computations from Nitrogen Isotherms", J. Am. Chem. Soc., 1951, 373-380, 73(1).
Beck et al., "A New Family of Mesoporous Molecular Sieves Prepared with Liquid Crystal Templates", J. Am. Chem. Soc., 1992, 10834-10843, 114, American Chemical Society.
Bhuiyan et al., "Kinetics Modelling of 2-Butene Metathesis Over Tungsten Oxide Containing Mesoporous Silica Catalyst", The Canadian Journal of Chemical Engineering, 2014, 1271-1282. 92.
Bhuiyan et al., "Metathesis of 2-Butene to Propylene over W-Mesoporous Molecular Sieves: A Comparative Study Between Tungsten Containing MCM-41 and SBA-15", Applied Catalysis A: General, 2013, 224-234, 467, Elsevier B.V.
Bin Hu, et al., "Highly Active Doped Mesoporous KIT-6 Catalysts for Metathesis of 1-Butene and Ethene to Propene: The Influence of Neighboring Environment of W Species", The Journal of Physical Chemistry, ACS Publication, 2013 American Chemical Society, pp. 26385-26395, USA.
Daniell et al., "Enhanced Surface Acidity in Mixed Alumina-Silicas: A Low-Temperature" FTIR Study:, 2000, 196, 247-260, Elsevier.
Do et al., "Zeolite Nanoclusters Coated onto the Mesopore Walls of SBA-15", J. Am. Chem. Soc., 2004, 14324-14325, 126, American Chemical Society.
International Search Report and Written Opinion dated Nov. 11, 2016 pertaining to International Application No. PCT/US2016/039025.
International Search Report and Written Opinion dated Sep. 14, 2016 pertaining to International Application No. PCT/US2016/039012.
International Search Report and Written Opinion dated Sep. 27, 2016 pertaining to International Application No. PCT/US2016/0038967.
International Search Report and Written Opinion dated Sep. 14, 2016 pertaining to International Application No. PCT/US2016/039013.
Jermy et al., "Utilization of ZSM-5/MCM-41 Composite as FCC Catalyst Additive for Enhancing Propylene Yield from VGO Cracking", J. Porous Mater, 2012, 499-509, 19, Springer.
Kawai et al., "Metaethesis of Halogen-Containing Olefin Over Re2O7/Al2O3 Catalyst Promited with Alkylmetal as a Cocatalyst", Journal of Molecular Catalysis A: Chemical, 1998, 133, 51-59.
Kumar et al., "Performance of Nano Crystalline H-ZSM-5 As Additive in FCC Catalyst: A Review", International Journal of Research in Engineering and Tehnology, May 2014, vol. 3, pp. 481-485.
Lwin et al., "Olefin Metathesis by Supported Metal Oxide Catalysts", ACS Catalysis, 2014, 2505-2520, 4, American Chemical Society.
Quignard et al., "Aryloxide Ligands in Metathesis of Olefins and Olefinic Esters: Catalytic Behaviour ofW(OAr)2Cl4 by SnMe4, Sn(n-Bu)4, Pb(n-Bu)4, MgNp2: synthesis of W(OAr)2Cl2(CHCMe3)(OR2) and W(OAr)2Cl(CHCMe3)(CH2CMe3)(OR2)", Journal of Molecular Catalysis, 1986, 36, 13-29.
Ruihua Gao, et al., "High-activity, single-site mesoporous WO3-MCF materials for the catalytic epoxidation of cycloocta-1,5-diene with aqueous hydrogen peroxide", Journal of Catalysis, 256, 2008, pp. 259-267, China.
Wang et al., "Synthesis and Structure of Silicalite-1/SBA-15 Composites Prepared by Carbon Templating and Crystallization", Journal of Materials Chemistry, 2007,4265-4273,17, The Royal Society of Chemistry 2007.
Wang et al., "Effect of Support Nature on WO3/SiO2 Structure and Butene-1 Metathesis", Applied Catalysis A: General, 2003, 25-37, 250, Elsevier B.V.
Zhao et al., "Effect of Tungsten Oxide Loading on Metathesis Activity of Ethene and 2-Butene Over WO3/SiO2 Catalysts" Transition Met Chem, 2009, 621-27, 34, Springer.
International Preliminary Report on Patentability dated Jan. 11, 2018—PCT/US2016/039012.
International Preliminary Report on Patentability dated Jan. 2, 2018—PCT/US2016/039012.
Puriwat, et al., "Elucidation of the basicity dependence of 1-butene isomerization on MgO/Mg(OH)s catalysts", Catalysis Communications, 2010, pp. 80-85.
International Search Report and Written opinion dated Mar. 28, 2018, pertaining to International Application No. PCT/US2018/013945, filed Jan. 17, 2018, 9 pages.
International Search Report and Written Opinion dated Apr. 24, 2018 pertaining to International Application No. PCT/US2018/014131, filed Jan. 18, 2018.
Harmse et al., "On the Product Formation in 1-Butene Metathesis over Supported Tungsten Catalysts", Catal. Lett, vol. 137, pp. 123-131, Apr. 2010.
Shaikh et al., "Self-Metathesis of Butenes to Propylene", Catalysis in Petroleum Refining & Petrochemicals, pp. 1-6, Dec. 7-8, 2015.
Debecker et al., "Preparation of MoO3/siO2-Al2O3 methathesis catalysts via wet impregnation with different Mo precursors", Journal of Molecular Catalysis A: Chemical , 340, pp. 65-76, 2011.
Wu et al., "Investigation on acidity of zeolites bound with silica and alumina", Studies in Surface Science and Catalysis, 143, pp. 217-225, 2002.
Debecker et al., "Aerosol route to nanostructured WO3—SiO2—Al2O3 methathesis catalysts: Toward higer propene yield", Applied Catalysis A: General 470, pp. 458-466, 2014.
International Search Report and Written Opinion pertaining to Application No. PCT/US2019/054377 dated Jan. 13, 2020.
International Search Report and Written Opinion dated Feb. 23, 2021 pertaining to International application No. PCT/US2020/058640 filed Nov. 3, 2020, 14 pgs.
International Search Report and Written Opinion dated May 31, 2021 pertaining to International application No. PCT/US2020/060438 filed Nov. 13, 2020, 12 pages.
International Search Report and Written Opinion pertaining to Application No. PCT/US2019/054378 dated Jan. 13, 2020.
Notification of Transmittal of the International Search Report and Written Opinion of the International Searching Authority, or the Declaration dated Nov. 14, 2022 pertaining to International application No. PCT/US2022/037792 filed Jul. 21, 2022, 29 pages.
Nath et al., A new united atom force field for a-olefins, Journal of Chemical Physics, Feb. 22, 2001, vol. 114, No. 8 (5 pages).

* cited by examiner

PROCESSES INTEGRATING HYDROCARBON CRACKING WITH METATHESIS FOR PRODUCING PROPENE

TECHNICAL FIELD

Embodiments of the present disclosure generally relate to systems and processes for upgrading hydrocarbons, in particular, systems and processes that integrate hydrocarbon cracking and metathesis for producing propene and other olefins from hydrocarbons.

BACKGROUND

Ethylene, propene, butene, butadiene, and aromatics compounds such as benzene, toluene and xylenes are basic intermediates for the petrochemical industry. These compounds can be produced through thermal cracking (steam cracking or steam pyrolysis) of petroleum gases and distillates such as naphtha, kerosene, or even gas oil. These compounds can also be produced through refinery fluidized catalytic cracking (FCC) processes, in which classical heavy feedstocks such as gas oils or residues are converted. Typical FCC feedstocks range from hydrocracked bottoms to heavy feed fractions such as vacuum gas oil and atmospheric residue; however, these feedstocks are limited. The second most important source for propene production is currently refinery propene from FCC units.

The worldwide increasing demand for light olefins remains a major challenge for many integrated refineries. In particular, the production of propene has attracted increased attention as pure olefin streams are considered the building blocks for polymer synthesis. The production of light olefins depends on several process variables, such as the feed type, operating conditions, or the type of catalyst. Despite the options available for producing a greater yield of propene, intense research activity in this field is still being conducted. These options include the use of high-severity fluidized catalytic cracking (HS-FCC) systems, developing more selective catalysts for the process, and enhancing the configuration of the process in favor of more advantageous reaction conditions and yields. The HS-FCC process is capable of producing yields of propene up to four times greater than the traditional fluid catalytic cracking unit and greater conversion levels for a range of petroleum steams. Other options include steam cracking, which can also convert hydrocarbons to olefins.

SUMMARY

However, hydrocarbon cracking systems, such as HS-FCC systems and steam cracking systems, can produce substantial amounts of C4+ compounds, such as mixed butenes (1-butene, trans-2-butene, cis-2-butene, isobutene) butane, and isobutane, as well as ethylene, pentene, and other C5+ compounds. Production of larger C5+ hydrocarbons, which may be of lesser value as chemical intermediates compared to propene, may reduce the selectivity and yield of propene, ethylene, or both, from the hydrocarbon cracking process.

Accordingly, ongoing needs exist for processes and systems for producing olefins, such as propene and ethylene, from hydrocarbon feedstocks at greater selectivity and yield of propene compared to conventional hydrocarbon cracking processes. Additionally, ongoing needs exist for processes and systems for producing olefins, such as propene, from a broader spectrum of hydrocarbon feedstocks, such as feedstocks including naphtha streams or gas condensate streams. The processes and systems of the present disclosure include a hydrocarbon cracking system, such as a fluidized catalytic cracking system or steam cracking system, with a downstream metathesis process. The hydrocarbon cracking system may be operable to catalytically or thermally crack the hydrocarbon feed to produce olefins, such as ethylene, propene, mixed butenes, and other C4+ compounds. A cracking C4 effluent, such as a C4 raffinate, from the hydrocarbon cracking process is further processed in metathesis system, which is a dual catalyst metathesis system that includes a metathesis catalyst and a cracking catalyst, to convert at least a portion of the mixed butenes to ethylene and propene through metathesis and cracking of the mixed butenes. The cracking C4 effluent can include 1-butene, trans-2-butene, cis-2-butene, isobutene, butane, isobutane, and 1,3-butadiene.

Propene continues to be of greater value in the market compared to ethylene. The processes of the present disclosure can improve the yield and selectivity for producing propene by controlling the ratio of butene isomers in the feed to the metathesis system. In particular, the systems and processes of the present disclosure include a selective hydrogenation and isomerization unit (SHIU) disposed between the hydrocarbon cracking system and the metathesis system. The SHIU contains a selective hydrogenation catalyst and is operable to convert 1,3-butadiene in the C4 effluent to 1-butene and to isomerize at least a portion of 1-butene in the C4 effluent or produced from hydrogenation of 1,3-butadiene to 2-butenes. The hydrogenation effluent from the SHIU can then be passed to the metathesis unit. The SHIU is operated at conditions such that the concentration of 2-butenes in the hydrogenation effluent is greater than or equal to the sum of the concentrations of 1-butene and isobutene in the hydrogenation effluent. The isobutene is not removed from the cracking C4 effluent or the hydrogenation effluent prior to metathesis. The presence of the isobutene and the concentration of 2-butenes greater than or equal to the sum of the concentrations of 1-butene and isobutene in the hydrogenation effluent may shift the selectivity of the metathesis process towards greater propene production and less ethylene production, thereby increasing the yield and selectivity of propene from the process compared to operating the metathesis unit without the presence of isobutene and with a concentration of 2-butene less than the combined concentrations of 1-butene and isobutene.

According to one or more aspects of the present disclosure, a process for producing olefins may include passing a hydrocarbon feed to a hydrocarbon cracking unit that cracks at least a portion of the hydrocarbon feed to produce a cracker effluent and passing the cracker effluent to a cracker effluent separation system that separates the cracker effluent to produce at least a cracking C4 effluent. The cracking C4 effluent may comprise at least 1-butene, 1,3-butadiene, and isobutene. The process may further comprise passing the cracking C4 effluent to a selective hydrogenation and isomerization unit that contacts the cracking C4 effluent with hydrogen in the presence of a selective hydrogenation catalyst to produce a hydrogenation effluent. Contacting the cracking C4 effluent with the hydrogen in the presence of the selective hydrogenation catalyst may hydrogenate 1,3-butadiene to 1-butene, n-butane, or both and isomerizes at least a portion of the 1-butene to 2-butenes. A concentration of 2-butenes in the hydrogenation effluent may be greater than or equal to a sum of a concentration of 1-butene and a concentration of isobutene in the hydrogenation effluent. The process may further comprise passing the hydrogenation effluent to a metathesis unit that contacts the hydrogenation effluent with a metathesis catalyst and a cracking catalyst downstream of the metathesis catalyst to produce a metathesis reaction effluent comprising at least propene. The contacting with the metathesis catalyst may cause metathesis of at least a portion of the 1-butene, 2-butenes, and isobutene in the hydrogenation effluent to produce a metathesis reaction product, and the contacting with the cracking catalyst may cause at least a portion of C5+ olefins produced through metathesis to undergo cracking reactions to produce propene, ethylene, or both.

According to one or more other aspects of the present disclosure, a system for producing olefins may include a hydrocarbon feed; a hydrocarbon cracking system in fluid communication with the hydrocarbon feed, the hydrocarbon cracking system comprising a hydrocarbon cracking unit and a cracker effluent separation system downstream of the hydrocarbon cracking unit; a selective hydrogenation and isomerization unit downstream of the cracker effluent separation system, the selective hydrogenation and isomerization unit comprising a selective hydrogenation catalyst; a metathesis unit downstream of the selective hydrogenation and isomerization unit, the metathesis unit comprising a metathesis catalyst disposed in a metathesis reaction zone and a cracking catalyst disposed in a cracking reaction zone downstream of the metathesis reaction zone; and a control system communicatively coupled to the hydrocarbon cracking unit, the cracker effluent separation system, the selective hydrogenation and isomerization unit, and the metathesis unit. The control system may comprise at least one processor, at least one memory module communicatively coupled to the at least one processor, and machine readable and executable instructions stored on the at least one memory module. The machine readable and executable instructions, when executed by the at least one processor, may cause the control system to automatically: operate the hydrocarbon cracking unit to thermally or catalytically crack at least a portion of a hydrocarbon feed to produce a cracker effluent comprising olefins; operate the cracker effluent separation system to separate the cracker effluent to produce at least a cracking C4 effluent comprising at least 1-butene, isobutene, and 1,3-butadiene; operate the selective hydrogenation and isomerization unit to contact the cracking C4 effluent with hydrogen in the presence of the selective hydrogenation catalyst to produce a hydrogenation effluent; maintain the selective hydrogenation and isomerization unit under operating conditions sufficient to convert the 1,3-butadiene to 1-butene and isomerize 1-butene to 2-butene so that a concentration of 2-butenes in the hydrogenation effluent is greater than or equal to a sum of a concentration of 1-butene and a concentration of isobutene in the hydrogenation effluent; and operate the metathesis system to contact the hydrogenation effluent with the metathesis catalyst and cracking catalyst to produce a metathesis reaction effluent comprising at least propene.

Additional features and advantages of the present disclosure will be set forth in the detailed description that follows, and in part will be readily apparent to those skilled in the art from that description or recognized by practicing the described subject matter, including the detailed description that follows, the claims, as well as the appended drawings.

BRIEF DESCRIPTION OF THE DRAWINGS

The following detailed description of specific aspects of the present disclosure can be best understood when read in conjunction with the following drawings, in which like structure is indicated with like reference numerals and in which.

Figure 1:
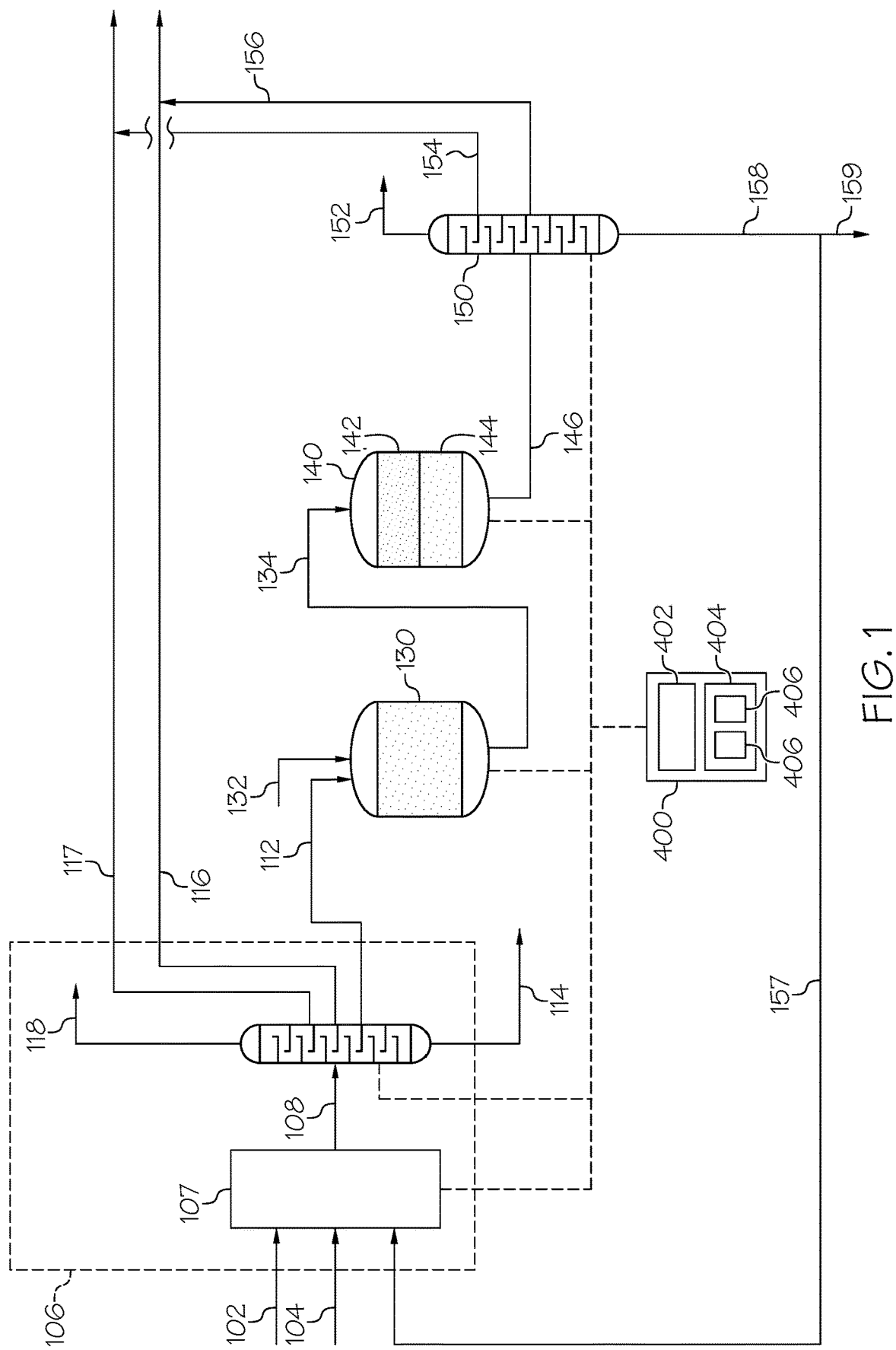
FIG. 1 schematically depicts a generalized flow diagram for a system for producing olefins, according to one or more embodiments shown and described in the present disclosure.

For purposes of describing the simplified schematic illustrations and descriptions in FIGS. 1-7, the numerous valves, control valves, temperature sensors, flow meters, pressure regulators, electronic controllers, pumps, compressors, heat exchangers, and the like that may be employed and well known to those of ordinary skill in the art of certain chemical processing operations may not be depicted. Further, accompanying components that are often included in typical chemical processing operations, such as valves, pipes, pumps, agitators, heat exchangers, condensers, boilers, instrumentation, internal vessel structures, or other subsystems may not be depicted. Though not depicted, it should be understood that these components are within the spirit and scope of the present embodiments disclosed. However, operational components, such as those described in the present disclosure, may be added to the embodiments described in this disclosure.

Arrows in the drawings refer to process streams. However, the arrows may equivalently refer to transfer lines, such as pipes or conduits, which may serve to transfer process streams between two or more system components. Additionally, arrows that connect to system components may define inlets or outlets in each given system component. The arrow direction corresponds generally with the major direction of movement of the materials of the stream contained within the physical transfer line signified by the arrow. Furthermore, arrows which do not connect two or more system components may signify a product stream which exits the depicted system component or a system inlet stream which enters the depicted system or system component.

Additionally, arrows in the drawings may schematically depict process steps of transporting a stream or composition from one system component to another system component. For example, an arrow from one system component pointing to another system component may represent "passing" a stream or composition to another system component, which may include the contents of a process stream "exiting" or being "removed" from one system component and "introducing" the contents of that product stream to another system component.

Reference will now be made in greater detail to various aspects of the present disclosure, some aspects of which are illustrated in the accompanying drawings.

DETAILED DESCRIPTION

The present disclosure is directed to systems and processes for producing olefins from a hydrocarbon feed. Referring to FIG. 1, one embodiment of a system 100 for producing olefins is schematically depicted. The system 100 may include a hydrocarbon feed 102, a hydrocarbon cracking system 106 in fluid communication with the hydrocarbon feed 102, a selective hydrogenation and isomerization unit (SHIU) 130 downstream of the hydrocarbon cracking system 106, and a metathesis unit 140 downstream of the SHIU 130. The hydrocarbon cracking system 106 may include a hydrocarbon cracking unit 107 and a cracker effluent separation system 110 downstream of the hydrocarbon cracking unit 107. The SHIU 130 comprises a selective hydrogenation catalyst. The metathesis unit 140 may include a metathesis catalyst disposed in a metathesis reaction zone 142 and a cracking catalyst disposed in a cracking reaction zone 144 downstream of the metathesis reaction zone 142.

The system 100 may include a control system 400 communicatively coupled to the hydrocarbon cracking unit 107, the cracker effluent separation system 110, the SHIU 130, and the metathesis system. The control system 400 may include at least one processor 402, at least one memory module 404 communicatively coupled to the at least one processor 402, and machine readable and executable instructions 406 stored on the at least one memory module 404. The machine readable and executable instructions 406, when executed by the at least one processor 402, may cause the control system 400 to automatically operate the hydrocarbon cracking unit 107 to thermally or catalytically crack at least a portion of a hydrocarbon feed 102 to produce a cracker effluent 108 comprising olefins; operate the cracker effluent separation system 110 to separate the cracker effluent 108 to produce at least a cracking C4 effluent 112 comprising 1-butene, isobutene, and 1,3-butadiene; operate the SHIU 130 to contact the cracking C4 effluent 112 with hydrogen 132 in the presence of the selective hydrogenation catalyst to produce a hydrogenation effluent 134; and operate a metathesis unit 140 of the metathesis system to contact the hydrogenation effluent 134 with the metathesis catalyst and cracking catalyst to produce a metathesis reaction effluent 146 comprising at least propene. The machine readable and executable instructions 406, when executed by the at least one processor 402, may cause the control system 400 to automatically maintain the SHIU 130 under operating conditions sufficient to convert the 1,3-butadiene to 1-butene and isomerize 1-butene to 2-butene so that a concentration of 2-butenes in the hydrogenation effluent 134 is greater than or equal to a sum of a concentration of 1-butene and a concentration of isobutene in the hydrogenation effluent 134.

Referring again to FIG. 1, the processes of the present disclosure for producing olefins may include passing the hydrocarbon feed 102 to the hydrocarbon cracking unit 107 that may crack at least a portion of the hydrocarbon feed 107 to produce the cracker effluent 108 and passing the cracker effluent 108 to the cracker effluent separation system 110 that may separate the cracker effluent 108 to produce at least the cracking C4 effluent 112 that comprises at least 1-butene, 1,3-butadiene, and isobutene. The processes may further include passing the cracking C4 effluent 112 to the SHIU 130 that contacts the cracking C4 effluent 112 with hydrogen 132 in the presence of a selective hydrogenation catalyst to produce the hydrogenation effluent 134. Contacting the cracking C4 effluent 112 with the hydrogen 132 in the presence of the selective hydrogenation catalyst hydrogenates 1,3-butadiene to 1-butene, n-butane, or both and isomerizes at least a portion of the 1-butene to 2-butenes. The concentration of 2-butenes in the hydrogenation effluent 134 is greater than or equal to a sum of a concentration of 1-butene and a concentration of isobutene in the hydrogenation effluent 134. The processes further include passing the hydrogenation effluent 134 to the metathesis unit 140 that may contact the hydrogenation effluent 134 with a metathesis catalyst and a cracking catalyst downstream of the metathesis catalyst to produce the metathesis reaction effluent 146 comprising at least propene. Contacting with the metathesis catalyst causes metathesis of at least a portion of the 1-butene, 2-butenes, and isobutene in the hydrogenation effluent 134 to produce a metathesis reaction product, and contacting with the cracking catalyst causes at least a portion of C5+ olefins produced through metathesis to undergo cracking reactions to produce propene, ethylene, or both.

The systems and processes of the present disclosure do not require removal of isobutene from the cracking C4 effluent 112 or from the hydrogenation effluent 134 prior to metathesis. The presence of the isobutene and the concentration of 2-butenes in the hydrogenation effluent 134 being greater than or equal to the sum of the concentrations of 1-butene and isobutene may shift the selectivity of the metathesis process towards greater propene production and less ethylene production, thereby increasing the yield and selectivity of propene from the process compared to operating the metathesis unit 140 without the presence of isobutene and with a concentration of 2-butene less than the combined concentrations of 1-butene and isobutene. Other features and benefits of the systems and processes of the present disclosure may become apparent from practicing the subject matter of the present disclosure.

The term "or", as used in the present disclosure, is inclusive; more specifically, the phrase "A or B" means "A, B, or both A and B." Exclusive "or" is designated in the present disclosure by terms such as "either A or B" and "one of A or B," for example.

The indefinite articles "a" and "an" are employed to describe elements and components of the present disclosure. The use of these articles means that one or at least one of these elements or components is present. Although these articles are conventionally employed to signify that the modified noun is a singular noun, as used herein the articles "a" and "an" also include the plural, unless otherwise stated in specific instances. Similarly, the definite article "the", as used in the present disclosure, also signifies that the modified noun may be singular or plural, again unless otherwise stated in specific instances.

As used throughout the present disclosure, the terms "upstream" and "downstream" refer to the positioning of components or units of the system 100 relative to a direction of flow of materials through the system 100. For example, a first component may be considered "upstream" of a second component if materials flowing through the system 100 encounter the first component before encountering the second component. Likewise, the second component is considered "downstream" of the first component if the materials flowing through the system 100 encounter the first component before encountering the second component.

As used throughout the present disclosure, reciting that a stream is passed "directly" from an upstream component to a downstream component may refer to passing the stream from the upstream component to the downstream component without passing the stream through an intervening unit operation operable to change the composition of the stream through chemical reaction or separation of one or more components. Intervening unit operations can include reactors and separation units but are not generally intended to include heat exchangers, valves, pumps, sensors, or other ancillary process equipment required for operation of a chemical process. Intervening unit operations are also not intended to include combining streams between the upstream component and downstream component or removing a slip stream having the same composition as the stream from which it is separated.

As used throughout the present disclosure, the term "fluid" may be used to refer to a flowable composition that includes gases, liquids, or a combination of these.

As used throughout the present disclosure, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), a plug flow reactor, a packed bed reactor, a fluidized bed reactor, continuous fluidized bed reactor, a riser reactor, downer reactor, or other type of reactor. One or more "reaction zones" may be disposed in a reactor. As used throughout this disclosure, a "reaction zone" may refer to a region where a particular reaction takes place in a reactor. For example, a packed bed reactor with multiple catalyst beds may have multiple reaction zones, where each reaction zone is defined by the region occupied by one of the catalyst beds. In another non-limiting example, a multi-stage catalyst reaction system may include multiple reactors, and each reactor may define a separate "reaction zone."

As used throughout the present disclosure, the terms "separation unit" and "separator" may be interchangeable and refer to any separation device that at least partially separates one or more chemicals that are mixed in a process stream from one another. For example, a separation unit may selectively separate differing chemical species from one another, forming one or more chemical fractions. Examples of separation units include, without limitation, distillation columns, fractionators, flash drums, knock-out drums, knock-out pots, centrifuges, cyclones, filtration devices, traps, scrubbers, expansion devices, adsorption units, membrane separation units, solvent extraction devices, and the like. As used throughout the present disclosure, the term "separation system" may refer to a system that can include one or a plurality of separation units.

It should be understood that separation units and separation systems described in this disclosure may not completely separate all of one chemical constituent from all of another chemical constituent. It should be understood that the separation units and separation systems described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided, or separated, into two or more process streams of different compositions. A process stream passed out of a separation unit or separation system may be designated using the name of a certain compound or class of compounds and may be considered to include a greater proportion of that certain compound or class of compounds relative to other streams passed out of the separation unit or separation system. It is understood, however, that the other streams passed out of the separation unit or separation system may also include some amounts of the certain compound or class of compounds.

As used throughout the present disclosure, the term "high-severity conditions" may refer to operating conditions in the HS-FCC system 200 (FIG. 2) that include temperatures of greater than or equal to 500 degrees Celsius (° C.) or greater, a weight ratio of cracking catalyst to hydrocarbon feed (catalyst to oil ratio) of equal to or greater than 5:1, and a residence time of less than or equal to 3 seconds (sec), all of which may be more severe than typical FCC reaction conditions. As used throughout the present disclosure, the term "residence time" may refer to the amount of time that the reactants are in contact with the catalyst at reaction conditions, such as at the reaction temperature, in a reaction system. As a non-limiting example, the residence time in a high-severity fluidized catalytic cracking reactor may refer to the time that the hydrocarbons of the hydrocarbon feed are in contact with the cracking catalyst at the reaction temperature.

As used throughout the present disclosure, the term "effluent" may refer to a stream that exits a system component such as a separation unit, a reactor, or reaction zone, following a particular reaction or separation, and generally has a different composition (at least proportionally) compared to the stream that entered the separation unit, reactor, or reaction zone.

As used throughout the present disclosure, a "catalyst" may refer to any substance that increases the rate of a specific chemical reaction. Catalysts described in this disclosure may be utilized to promote various reactions, such as, but not limited to, cracking reactions, hydrogenation reactions, metathesis reactions, isomerization reactions, hydration reactions, or other chemical reaction.

As used throughout the present disclosure, "cracking" may generally refer to a chemical reaction where a molecule having carbon to carbon bonds is broken into more than one molecule by the breaking of one or more of the carbon to carbon bonds, or is converted from a compound which includes a cyclic moiety, such as a cycloalkane, cycloalkene, naphthalene, an aromatic or the like, to a compound which does not include a cyclic moiety or contains fewer cyclic moieties than prior to cracking.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream of effluent are disclosed as passing from one system component to another when a stream or effluent comprising that component is disclosed as passing from that system component to another. For example, a disclosed "cracking C4 effluent" passing from a first system component to a second system component should be understood to equivalently disclose the various constituents of the "cracking C4 effluent" passing from the first system component to the second system component.

As used throughout the present disclosure, the terms "butenes" or "mixed butenes" may be used interchangeably and may refer to combinations of one or a plurality of isobutene, 1-butene, trans-2-butene, or cis-2-butene. As used throughout the present disclosure, the term "normal butenes" may refer to a combination of one or a plurality of 1-butene, trans-2-butene, or cis-2-butene. As used throughout the present disclosure, the term "2-butenes" may refer to trans-2-butene, cis-2-butene, or a combinations of these.

As used throughout the present disclosure, the term "C4" may be used to refer to compositions or streams comprising compounds having 4 carbon atoms, the term "C4+" may be used to refer to compositions or streams comprising compounds having 4 or more than 4 carbon atoms, and the term "C5+" may be used to refer to compositions or streams comprising compounds having 5 or more than 5 carbon atoms.

Referring again to FIG. 1, the system 100 for producing olefins may include the hydrocarbon cracking system 106, the selective hydrogenation and isomerization unit 130 (SHIU 130) downstream of the hydrocarbon cracking system 106, and the metathesis system 140 downstream of the SHIU 130. The hydrocarbon cracking system 106 may include a hydrocarbon cracking unit 107 and a cracker effluent separation system 110 downstream of the hydrocarbon cracking unit 107. The hydrocarbon cracking unit 107 may be operable to crack at least a portion of the hydrocarbons from a hydrocarbon feed 102 to produce a cracker effluent 108. The hydrocarbon cracking unit 107 may be a high-severity fluid catalytic cracking (HS-FCC) unit or a steam cracking unit. The cracker effluent 108 is passed to the cracker effluent separation system 110 that is operable to separate the cracker effluent 108 to produce at least the cracker C4 effluent 112 and one or more other effluents.

Hydrocarbon Feed

The hydrocarbon feed 102 may generally include a mixture of hydrocarbon materials. The hydrocarbon materials of the hydrocarbon feed 102 may include hydrocarbons derived from crude oil. As used in this disclosure, the term "crude oil" may be understood to mean a mixture of petroleum liquids and gases, including impurities such as sulfur-containing compounds, nitrogen-containing compounds and metal compounds, as distinguished from fractions of crude oil. The hydrocarbon feed 102 may include, but is not limited to, crude oil, vacuum residue, tar sands, bitumen, atmospheric residue, vacuum gas oils, demetalized oils, naphtha streams, gas condensate streams, or combinations of these materials. The hydrocarbon feed 102 may include one or a plurality of non-hydrocarbon constituents, such as one or more heavy metals, sulphur compounds, nitrogen compounds, inorganic components, or other non-hydrocarbon compounds. In embodiments, the hydrocarbon feed 102 may be a heavy oil, such as but not limited to crude oil, vacuum residue, atmospheric residue, tar sands, bitumen, vacuum gas oils, demetalized oils, or combinations of these.

In embodiments, the hydrocarbon feed 102 may be a naphtha stream, a gas condensate stream, or a combination of these. As used in the present disclosure, the term "naphtha" may refer to an intermediate hydrocarbon composition derived from crude oil refining and having a boiling point temperature of from 35° C. to 200° C. Naphtha streams may include paraffinic, naphthenic, and aromatic hydrocarbons having from 4 to 11 carbon atoms. In embodiments, the hydrocarbon feed 102 may be a naphtha stream comprising an Arab Extra Light (AXL) feedstock. As used in the present disclosure, the term "gas condensate" may refer to a mixture of liquid hydrocarbons having a specific gravity of from 0.5 to 0.8 and derived from raw natural gas produced from natural gas fields. Gas condensates may include paraffinic hydrocarbons having from 3 to 12 carbon atoms and lesser amounts of naphthenic and aromatic compounds compared to naphtha streams. Hydrocarbons with greater than 12 carbon atoms may also be present in gas condensates. The gas condensate may include at least 70 weight percent (wt. %), at least 75 wt. %, or even at least 80 wt. % hydrocarbons having a boiling point temperatures less than 265° C. The gas condensates may include the greater boiling hydrocarbons recovered from raw natural gas as a condensate in a natural gas processing plant. In embodiments, the gas condensate may be a Khuff gas condensate recovered from natural gas extracted from the Khuff reservoir in Saudi Arabia. Table 1 provides boiling point profile data for Khuff gas condensate.

TABLE 1

Boiling Point Temperature Profile for Khuff Gas Condensate

| Boiling Point (BP) Temperature Range | | Weight | Cummulative | Volume |
|---|---|---|---|---|
| Initial BP (° C.) | Final BP (° C.) | Percent wt. % | Weight Percent wt. % | Percent vol. % |
| C5 (35) | 70 | 12.9 | 12.9 | 15.36 |
| 70 | 185 | 47.32 | 60.22 | 48.15 |
| 185 | 265 | 19.9 | 80.12 | 18.79 |
| 265 | 345 | 12.14 | 92.26 | 10.99 |
| 345 | 460 | 6.87 | 99.13 | 6.04 |
| 460 | 565 | 0.29 | 99.42 | 0.25 |
| 565 | 1000 | 0.56 | 99.98 | 0.41 |

One or more supplemental feed streams (not shown) may be added to the hydrocarbon feed 102 prior to introducing the hydrocarbon feed 102 to the hydrocarbon cracking system 106 or introduced independently to the hydrocarbon cracking system 106 in addition to the hydrocarbon feed 102. For example, the hydrocarbon feed 102 may include a naphtha stream, a gas condensate, or a combination of these, and a supplemental stream, such as one or a plurality of a vacuum residue, atmospheric residue, vacuum gas oils, demetalized oils, or other hydrocarbon streams, or combinations of these materials, may be combined with the hydrocarbon feed 102 introduced independently to the hydrocarbon cracking system 106.

Hydrocarbon Cracking System

Referring again to FIG. 1, the hydrocarbon feed 102 is introduced to the hydrocarbon cracking system 106, which includes the hydrocarbon cracking unit 107 and the cracker effluent separation system 110 downstream of the hydrocarbon cracking unit 107. As previously discussed, the hydrocarbon cracking unit 107 can be an HS-FCC unit or a steam cracking unit.

Figure 2:
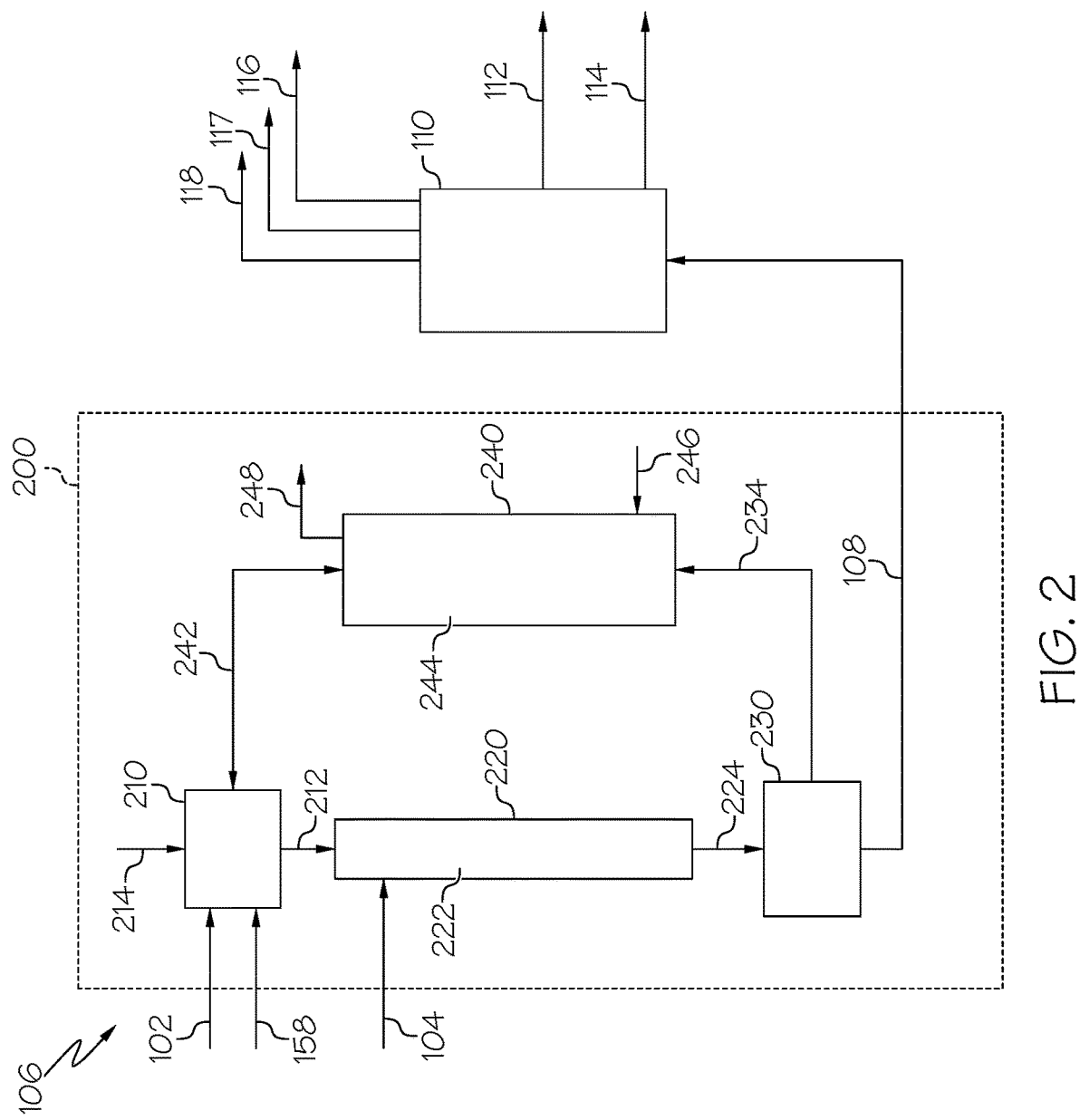
FIG. 2 schematically depicts a generalized flow diagram for a high-severity fluidized catalytic cracking (HS-FCC) system, according to one or more embodiments shown and described in the present disclosure.

Referring now to FIG. 2, a generalized flow diagram of one embodiment of an HS-FCC unit 200 and is schematically depicted. The HS-FCC unit 200 may include a mixing zone 210, an HS-FCC reactor 220 downstream of the mixing zone 210, a cracking catalyst separator 230 downstream of the HS-FCC reactor 220, and a cracking catalyst regenerator 240. The mixing zone 210 may be operable to receive the hydrocarbon feed 102, and any optional supplemental feed streams, and combine the hydrocarbon feed 102 with a cracking catalyst to form a mixed catalyst hydrocarbon stream 212. The mixing zone 210 may also receive any recycle streams, such as but not limited to a metathesis C4+ effluent 158 from the metathesis system 140. The cracking catalyst may include regenerated cracking catalyst 242, new cracking catalyst 214, or any combination of regenerated catalyst 242 and new cracking catalyst 214. For example, new cracking catalyst 214 may be added to the mixing zone 210 during initial startup of the HS-FCC unit 200 or during steady-state operation to replenish cracking catalyst lost due to attrition or removed due to permanent deactivation.

The cracking catalyst used in the HS-FCC unit 200 may include one or a plurality of fluid catalytic cracking catalysts suitable for use under the high-severity conditions in the HS-FCC reactor 220. The cracking catalyst may be a heat carrier and may provide heat transfer to the hydrocarbon feed 102 in the HS-FCC reactor 220 when operated at high-severity conditions. The cracking catalyst may also have a plurality of catalytically active sites, such as acidic sites that promote the cracking reactions. Examples of fluid catalytic cracking catalysts suitable for use in the HS-FCC unit 200 may include, without limitation, zeolites, silica-alumina catalysts, carbon monoxide burning promoter additives, bottoms cracking additives, light olefin-producing additives, other catalyst additives, or combinations of these components. Zeolites that may be used as at least a portion of the cracking catalyst may include, but are not limited to, Y, REY, USY, RE-USY zeolites, or combinations of these. The cracking catalyst may also include a shaped-selective catalyst additive, such as ZSM-5 zeolite crystals or other pentasil-type catalyst structures, which are often used in other FCC processes to produce light olefins, increase FCC gasoline octane, or both. In one or more embodiments, the catalyst may include a mixture of a ZSM-5 zeolite crystals and the cracking catalyst zeolite and matrix structure of a typical FCC cracking catalyst. In one or more embodiments, the catalyst may be a mixture of Y and ZSM-5 zeolite catalysts embedded with clay, alumina, and binder.

In embodiments, at least a portion of the cracking catalyst may be modified to include one or more rare earth elements (15 elements of the Lanthanide series of the International Union of Pure and Applied Chemistry (IUPAC) Periodic Table plus scandium and yttrium), alkaline earth metals (Group 2 of the IUPAC Periodic Table), transition metals, phosphorus, fluorine, or any combination of these, which may enhance olefin yield in the HS-FCC unit 200. Transition metals may include "an element whose atom has a partially filled d sub-shell, or which can give rise to cations with an incomplete d sub-shell" [IUPAC, Compendium of Chemical Terminology, 2nd ed. (the "Gold Book") (1997). Online corrected version: (2006-) "transition element"]. One or more transition metals or metal oxides may also be impregnated onto the catalyst. Metals or metal oxides may include one or more metals from Groups 6-10 of the IUPAC Periodic Table.

Referring again to FIG. 2, the hydrocarbon feed 102 and the cracking catalyst may be mixed in the mixing zone 210 to produce a mixed catalyst hydrocarbon stream 212 having a weight ratio of the cracking catalyst to hydrocarbons from the hydrocarbon feed 102 (catalyst to hydrocarbon weight ratio) sufficient for high-severity fluidized catalytic cracking, such as greater than or equal to 5:1, greater than or equal to 10:1, greater than or equal to 15:1, or even greater than or equal to 25:1. When the weight ratio of the cracking catalyst to hydrocarbons is less than 5:1, the conversion of hydrocarbons through catalytic cracking may be reduced due to lesser reactive catalyst sites available in the reactor. This can lead to a shift to a greater degree of thermal cracking relative to catalytic cracking, which can change the composition of the cracking reaction effluent. Additionally, the mixed catalyst hydrocarbon stream 212 may have a weight ratio of cracking catalyst to hydrocarbons from the hydrocarbon feed 102 of less than or equal to 40:1, less than or equal to 35:1, less than or equal to 30:1, less than or equal to 25:1, less than or equal to 15:1, or less than or equal to 10:1.

The mixed catalyst hydrocarbon stream 212 may be passed from the mixing zone 210 to the HS-FCC reactor 220. The HS-FCC reactor 220 may be a downflow reactor or "downer" reactor in which the mixed catalyst hydrocarbon stream 212 flows from the mixing zone 210 vertically downward through the cracking reaction zone 222 of the HS-FCC reactor 220. Steam 104 may be introduced to the top portion of the HS-FCC reactor 220 to provide additional heating to the mixed catalyst hydrocarbon stream 212. Although shown in FIG. 2 as being a "downer" reactor, the HS-FCC reactor 220 may also be a riser reactor in which the mixed catalyst hydrocarbon stream 212 flows upward through the HS-FCC reactor 220. The HS-FCC reactor 220 may define a cracking reaction zone 222 in which the hydrocarbons from the hydrocarbon feed 102 are contacted with the cracking catalyst under high-severity conditions, which may cause at least a portion of the hydrocarbons from the hydrocarbon feed 102 to react, such as undergoing at least a cracking reaction, to produce an HS-FCC reactor outlet stream 224, which may be a mixture of a cracking reaction products and used cracking catalyst. The cracking reaction products may include olefins, such as but not limited to ethylene, propene, mixed butenes, C5+ olefins, and combinations of these. Used cracking catalyst may refer to cracking catalyst having decreased catalytic activity (ability to promote the cracking reactions) compared to new or regenerated cracking catalyst. The reduced catalytic activity of the used cracking catalyst may be due to coke deposits, reduced temperature, or a combination of both.

The HS-FCC reactor 220 may be operated at high-severity conditions. The HS-FCC reactor 220 may be operated at a temperature of the cracking reaction zone 222 of from 500° C. to 800° C., from 500° C. to 700° C., from 500° C. to 650° C., from 500° C. to 600° C., from 550° C. to 800° C., from 550° C. to 700° C., from 550° C. to 650° C., from 550° C. to 630° C., from 550° C. to 600° C., from 600° C. to 800° C., from 600° C. to 700° C., or from 600° C. to 650° C. The temperature of the cracking reaction zone 222 in the HS-FCC reactor 220 may be maintained by heating the cracking catalyst to a catalyst temperature greater than the temperature in the cracking reaction zone 222 prior to mixing the cracking catalyst with the hydrocarbon feed 102 to produce the mixed catalyst hydrocarbon stream 212. In embodiments, steam 104 may be introduced to the HS-FCC reactor 220 to maintain the temperature in the cracking reaction zone 222.

The flowrate of the mixed catalyst hydrocarbon stream 212 through the cracking reaction zone 222 of the HS-FCC reactor 220 may be sufficient to produce a residence time of the hydrocarbons from the hydrocarbon feed 102 in contact with the cracking catalyst at reaction temperatures of less than or equal to 3 seconds (sec), such as less than or equal to 2.5 sec, less than or equal to 2.0 sec, or even less than or equal to 1.5 sec. When the residence time is greater than 3 seconds at the reaction temperature, excessive thermal cracking may occur, which may overly crack the hydrocarbons from the hydrocarbon feed 102 and reduce the selectivity towards olefins, such as propene, ethylene, and mixed butenes. The residence time of the mixed catalyst hydrocarbon stream 212 in the cracking reaction zone 222 of the HS-FCC reactor 220 may be greater than or equal to 0.2 sec, greater than or equal to 0.4 sec, or even greater than or equal to 1.0 sec. When the residence time is less than about 0.2 seconds, insufficient catalytic cracking may occur, which may result is decreased selectivity to olefins. The residence time of the mixed catalyst hydrocarbon stream 212 in the cracking reaction zone 222 of the HS-FCC reactor 220 may be from 0.2 sec to 3 sec, from 0.2 sec to 2.5 sec, from 0.2 sec to 2 sec, from 0.2 sec to 1.5 sec, from 0.4 sec to 3 sec, from 0.4 sec to 2.5 sec, or from 0.4 sec to 2 sec, from 0.4 sec to 1.5 sec, from 1.0 sec to 3 sec, from 1.0 sec to 2.5 sec, from 1.0 sec to 2 sec, or from 2 sec to 3 sec.

Referring again to FIG. 2, the HS-FCC reactor outlet stream 224 may be passed from the HS-FCC reactor 220 to the cracking catalyst separator 230 disposed downstream of the HS-FCC reactor 220. The cracking catalyst separator 230 separates the HS-FCC reactor outlet stream 224 into a used cracking catalyst stream 234 and a cracking reaction effluent 232. The cracking catalyst separator 230 may include a gas-solid separator, such as but not limited to cyclones, deflectors, or other device operable to mechanically separate the used cracking catalyst from the cracking reaction products. The cracking catalyst separator 230 may also include a stripping zone (not shown), in which a stripping gas, such as steam, is passed through the used cracking catalyst to remove at least some of the residual portion of the cracking reaction products retained by the used cracking catalyst. The stripping gases and cracking reaction products may be combined to form the cracker effluent 108, which can be passed downstream to the cracker effluent separation system 110.

The used cracking catalyst stream 234 may be passed to the cracking catalyst regenerator 240, which is operable to regenerate the used cracking catalyst stream 234 to produce the regenerated catalyst 242. Combustion gases 246 may be introduced to a regeneration zone 244 of the cracking catalyst regenerator 240. The combustion gases 246 may include one or more of combustion air, oxygen, fuel gas, fuel oil, or any combinations of these. In the regeneration zone 244, at least a portion of the coke deposited on the used cracking catalyst in the HS-FCC reactor 220 may oxidize (combust) in the presence of the combustion gases 246 to form flue gases, such as but not limited to carbon dioxide, carbon monoxide, water, or other flue gas.

Oxidation of the coke deposits produces heat, which may be transferred to and retained by the regenerated catalyst 242. Thus, regeneration of the used cracking catalyst may include increasing the temperature of the regenerated catalyst 242 above the operating temperature of the HS-FCC reactor 220 in addition to removing coke deposits. In embodiments, a combustion fuel such as but not limited to fuel gas or fuel oil, may be introduced to the regeneration zone 244 of the cracking catalyst regenerator 240 to increase the heat transferred to the regenerated catalyst 242. The regenerated catalyst 242 may be passed from the cracking catalyst regenerator 240 to the mixing zone 210. The cracking catalyst regenerator 240 may include one or a plurality of catalyst hoppers (not shown) in which the regenerated catalyst 242 may accumulate before being combined with the hydrocarbon feed 102 in the mixing zone 210.

The HS-FCC unit 200 is shown in FIG. 2 as comprising a single HS-FCC reactor 220. However, the HS-FCC unit 200 may also include a plurality of HS-FCC reactors 220 operated in parallel or in series. When the HS-FCC unit 200 includes a plurality of HS-FCC reactors 220, the HS-FCC unit 200 may also include a plurality of mixing zones 210, a plurality of cracking catalyst separators 230, a plurality of cracking catalyst regenerators 240, or combinations of these.

Figure 3:
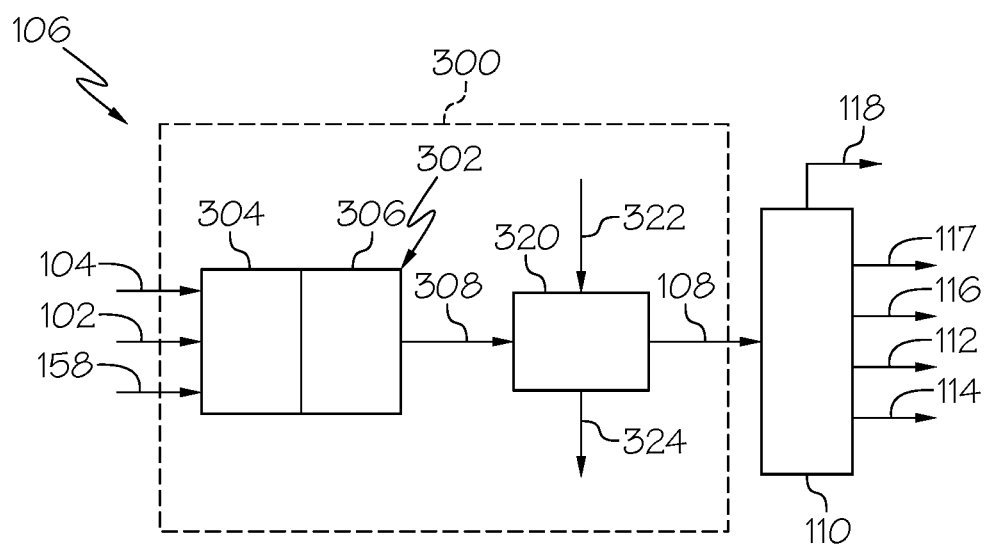
FIG. 3 schematically depicts a generalized flow diagram for a steam cracking system, according to one or more embodiments shown and described in the present disclosure.

Alternatively or additionally, the hydrocarbon cracking system 100 may include a steam cracking unit. Referring now to FIG. 3, a generalized flow diagram of one embodiment of a hydrocarbon cracking system 106 comprising a steam cracking unit 300 is schematically depicted. The steam cracking unit 300 may include a steam cracking reactor 302. The cracker effluent separation system 110 may be disposed downstream of the steam cracking reactor 302. The steam cracking system 300 may additionally include a heat exchanger 320 disposed between the steam cracking reactor 302 and the cracker effluent separation system 110. The steam cracking reactor 302 may be operable to heat the hydrocarbon feed 102 and contact the hydrocarbon feed 102 with steam 104 at a reaction temperature sufficient to cause at least a portion of the hydrocarbons from the hydrocarbon feed 102 to undergo thermal cracking to produce the cracker effluent 108 comprising olefins.

The hydrocarbon feed 102 and steam 104 may be passed directly to the steam cracking reactor 302. Other hydrocarbon containing streams, such as the metathesis C4+ effluent 158, metathesis C5+ effluent 174, or other recycle streams, may also be passed to the steam cracking reactor 302. The steam cracking reactor 302 may include a convection zone 304 and a pyrolysis zone 306 downstream of the convection zone 304. At least the hydrocarbon feed 102 and the steam 104 may pass into the convection zone 304. The flowrate of steam 104 passed into the convection zone 304 may be sufficient to conduct steam pyrolysis in the pyrolysis zone 306 downstream of the convection zone 304. The flowrate of steam 104 into the convection zone 304 may be sufficient to maintain a mass ratio of steam to hydrocarbons in the steam cracking reactor 302 of from 0.3:1 to 2:1. In the convection zone 304, the hydrocarbon feed 102 (and any other hydrocarbon streams passed to the convection zone 304) may be pre-heated to a pre-heat temperature. The pre-heat temperature of the convection zone 304 may be from 400° C. to 650° C.

The contents present in the convection zone 304 (at least the hydrocarbon feed 102 and the steam 104) may be passed to the pyrolysis zone 306 downstream of the convection zone 304. In the pyrolysis zone 306, at least the hydrocarbon feed 102 any another other hydrocarbons introduced to the steam cracking reactor 302 may be contacted with the steam 104 at reaction conditions sufficient to cause at least a portion of the hydrocarbons to undergo steam cracking (also known as steam pyrolysis) to produce a pyrolysis zone effluent 308. The pyrolysis zone 306 may operate at a temperature of from 700° C. to 900° C. The pyrolysis zone 306 may operate with a residence time of from 0.05 seconds to 2 seconds, where the residence time is the duration of time that the hydrocarbons are in contact with the steam at the reaction temperature of from 700° C. to 900° C. The mass ratio of steam 104 to hydrocarbons in the pyrolysis zone 306 may be from about 0.3:1 to about 2:1. The pyrolysis zone effluent 308 may exit the pyrolysis zone 306 of the steam cracking reactor 302 and may be passed through a heat exchanger 320 downstream of the steam cracking reactor 302. In the heat exchanger 320, a process fluid 322, such as water, pyrolysis fuel oil, or other process stream, may cool the pyrolysis zone effluent 308 to form the cracker effluent 108. In embodiments, the hydrocarbon cracking system 106 may include one or more HS-FCC units 200, one or more steam cracking units 300, or a combination of both.

Whether produced by the HS-FCC unit 200, the steam cracking unit 300, or a combination of both, the cracker effluent 108 may include a mixture of cracked hydrocarbon-based materials which may be separated into one or more petrochemical products included in one or more system product streams. For example, the cracker effluent 108 may include at least mixed butenes (1-butene, trans-2-butene, cis-2-butene, isobutene, or combinations of these). The cracker effluent 108 may also include other olefins, such as but not limited to ethylene, propylene, 1,3-butadiene, C5+ olefins, or combinations of these; light gases, such as but not limited to methane, hydrogen, steam, stripping gases, or combinations of these; saturated hydrocarbons, such as but not limited to ethane, propane, butane, isobutane, C5+ alkanes, or combinations of these; and aromatic compounds, such as but not limited to benzene, toluene, ethylbenzene, xylenes, or other aromatic compounds. The cracker effluent 108 may also include one or a plurality of fuel oil, gasoline, light cycle oil (LCO, 216° C.-343° C.), heavy cycle oil (HCO, >343° C.), or combinations of these. Other compounds may also be present in the cracker effluent 108 depending on the composition of the hydrocarbon feed 102 and operating conditions of the hydrocarbon cracking unit 107.

Referring to FIGS. 1-3, the cracker effluent 108 may be passed from the hydrocarbon cracking unit 107 (HS-FCC unit 200, steam cracking unit 300, or both) to the cracker effluent separation system 110. The cracker effluent separation system 110 may be fluidly coupled to the hydrocarbon cracking unit 107 such that the cracker effluent 108 can be passed directly from the hydrocarbon cracking unit 107 to the cracker effluent separation system 110. The cracker effluent separation system 110 may be operable to separate the cracker effluent 108 into a plurality of cracking effluent streams that include at least a cracking C4 effluent 112. The cracker effluent separation system 110 may include one or a plurality of separation units operable to separate the cracker effluent 108 into a plurality of cracking effluents. Separation units may include, but are not limited to, flash drums, high-pressure separators, distillation units, fractional distillation units, condensing units, strippers, quench units, debutanizers, depropanizers, de-ethanizers, or combinations of these. In embodiments, the cracker effluent separation system 110 may include a fractional distillation unit operable to separate the cracker effluent 108 to produce at least the cracking C4 effluent 112.

The cracker effluent separation system 110 may also be operable to separate the cracker effluent 108 into the cracking C4 effluent 112 and one or more of a greater boiling effluent 114, a cracking propene effluent 116, a cracking ethylene effluent 117, light gases 118, or combinations of these. The greater boiling effluent 114 may include constituents of the cracker effluent 108 having a boiling point temperature greater than the boiling point temperatures of the constituents of the cracking C4 effluent 112. The greater boiling effluent 114 may include one or a plurality of fuel oil, gasoline, pentane, other C5+ hydrocarbons, light cycle oil (LCO, having a boiling point temperature of 216° C. to 343° C.), heavy cycle oil (HCO, having a boiling point temperature of greater than 343° C.), other compounds having boiling points temperatures of C5+, or combinations of these. The greater boiling effluent 114 may also include small amounts of C4 hydrocarbons not separated into the cracking C4 effluent 112.

The cracking propene effluent 116 may include propene as a primary component. The cracking propene effluent 116 may include at least 90%, at least 95%, at least 98%, or even at least 99% by weight of the pentene from the cracker effluent 108. The cracking ethylene effluent 117 may include ethylene as a primary component. The cracking ethylene effluent 117 may include at least 90%, at least 95%, at least 98%, or even at least 99% by weight of the ethylene from the cracker effluent 108. The light gases 118 may include lesser molecular weight gases from the cracking reaction effluent, such as but not limited to methane, hydrogen, or other gases having a boiling point temperature less than ethylene and propene. One or a plurality of the greater boiling effluent 114, cracking propene effluent 116, cracking ethylene effluent 117, light gases 118, or combinations of these may be passed to one or more additional downstream unit operations for further processing. For example, the greater boiling effluent 114 may be passed to another separation unit for separation into one or a plurality of a gasoline stream, a fuel oil stream, a light cycle oil stream, a heavy cycle oil stream, other stream, or combinations of these. Steam may also be recovered from the cracker effluent 108.

The cracking C4 effluent 112 may include one or a plurality of n-butane, isobutane, 1,3-butadiene, mixed butenes (1-butene, trans-2-butene, cis-2-butene), isobutene, or combinations of these. The cracking C4 effluent 112 may also include small amounts of one or more other compounds present in the cracker effluent 108. The cracking C4 effluent 112 may include at least 90%, at least 95%, at least 98%, or even at least 99% by weight of the C4 compounds from the cracker effluent 108. The cracking C4 effluent 122 may include up to 60 wt. % 1,3-butadiene, such as from 1 wt. % to 60 wt. %, or from 10 wt. % to 50 wt. % 1,3-butadiene, based on the total weight of the cracking C4 effluent 122.

Selective Hydrogenation and Isomerization Unit (SHIU)

Referring again to FIG. 1, the cracking C4 effluent 112 may be passed to the selective hydrogenation and isomerization unit 130 (SHIU 130) disposed downstream of the hydrocarbon cracking system 106, such as downstream of the cracker effluent separation system 110. In embodiments, the SHIU 130 may be fluidly coupled to an outlet of the cracking effluent separation system 110 so that the cracking C4 effluent 112 can be passed directly from the cracking effluent separation system 110 to the SHIU 130 without passing through any intervening reactors or separation units. In embodiments, the cracking C4 effluent 112 may be passed through a guard bed (not shown) comprising a catalyst or other material for removal of impurities, such as but not limited to mercaptans, hydrogen sulfide, disulfide compounds, carbonyl sulfides, chlorides, heavy metals, and other metal impurities. The cracking C4 effluent 112 is passed from the cracking effluent separation system 110 to the SHUI 130 without removing the isobutene from the cracking C4 effluent 112.

As previously discussed, the cracking C4 effluent 112 may include 1,3-butadiene, which may produce unwanted metathesis products when contacted with the metathesis catalyst in the metathesis unit 140. The cracking C4 effluent 112 may include up to 60 wt. % 1,3-butadiene, such as from 1 wt. % to 60 wt. %, or from 10 wt. % to 50 wt. % 1,3-butadiene, based on the total weight of the cracking C4 effluent 112. As previously discussed, the cracking C4 effluent 112 may further include isobutene, 1-butene, and 2-butenes as well as other C4 hydrocarbons. The SHIU 130 may be operable contact the cracking C4 effluent 112 with hydrogen in the presence of a selective hydrogenation effluent under conditions sufficient to convert 1,3-butadiene to 1-butene and isomerize at least a portion of 1-butene to 2-butenes.

The SHUI 130 may include one or a plurality of hydrogenation reactors, such as 1, 2, 3, or more than 3 hydrogenation reactors. When the SHIU 130 includes a plurality of hydrogenation reactors, the hydrogenation reactors may be operated in series or in parallel. In embodiments, the SHUI 130 may include two hydrogenation reactors in series to achieve more than 99% conversion of 1,3-butadiene such that the concentration of 1,3-butadiene in the hydrogenation effluent 134 is less than or equal to 5,000 parts per million by weight based on the total weight of the hydrogenation effluent 134. Each of the hydrogenation reactors of the SHIU 130 may include at least one hydrogenation reaction zone comprising the selective hydrogenation catalyst. Each of the hydrogenation reactors of the SHIU 130 may be a fixed bed reactor comprising the selective hydrogenation catalyst.

The selective hydrogenation catalyst may include a catalytic metal supported on an alumina catalyst support. Alumina refers to aluminum oxide having formula $Al_2O_3$. In embodiments, the alumina catalyst support may be gamma alumina, such as but not limited to gamma alumina spheres. The catalytic metal may include one or more metals in Groups 8-11 of the International Union of Pure and Applied Chemistry periodic table of elements (IUPAC periodic table). In particular, the catalytic metal of the selective hydrogenation catalyst may include one or more of platinum, rhodium, palladium, ruthenium, cobalt, nickel, copper, or combinations of these metals. In embodiments, the catalytic metal may include palladium, platinum, nickel, copper, or combinations of these. The catalytic metal may be dispersed across surfaces of the alumina catalyst support, such as dispersed across surfaces of the alumina catalyst support that are accessible to reactants.

The selective hydrogenation catalyst may include from 0.01 wt. % to 1 wt. %, from 0.01 wt. % to 0.75 wt. %, from 0.01 wt. % to 0.5 wt. %, from 0.1 wt. % to 1 wt. %, from 0.1 wt. % to 0.75 wt. %, from 0.1 wt. % to 0.5 wt. %, from 0.3 wt. % to 1 wt. %, from 0.3 wt. % to 0.75 wt. %, or from 0.3 wt. % to 0.5 wt. % catalytic metal based on the total weight of the selective hydrogenation catalyst. In embodiments, the selective hydrogenation catalyst comprises palladium on an alumina catalyst support. A selective hydrogenation catalyst comprising palladium on an alumina catalyst support can produce high conversion of butadiene with a high selectivity to 2-butene from the selective hydrogenation process compared to other catalytic metals. This may allow the effluent from selective hydrogenation to have a great concentration of 2-butene compared to the concentration of 1-butene. The selective hydrogenation catalyst may include from 0.01 wt. % to 1 wt. %, from 0.01 wt. % to 0.75 wt. %, from 0.01 wt. % to 0.5 wt. %, from 0.1 wt. % to 1 wt. %, from 0.1 wt. % to 0.75 wt. %, from 0.1 wt. % to 0.5 wt. %, from 0.3 wt. % to 1 wt. %, from 0.3 wt. % to 0.75 wt. %, or from 0.3 wt. % to 0.5 wt. % palladium based on the total weight of the selective hydrogenation catalyst. When the amount of catalytic metal is in the range of from 0.01 wt. % to 1, such as from 0.1 wt. % to 0.75 wt. %, or even from 0.3 wt. % to 5 wt. %, the 1,3-butadiene may be hydrogenated to 1-butene without over-hydrogenating the olefins and may result in sufficient isomerization of 1-butene to 2-butene so that the concentration of 2-butene is greater than the sum of the concentrations of 1-butene and isobutene in the hydrogenation effluent 134. The selective hydrogenation catalyst may enable selective hydrogenation of butadiene and other dienes without the need for pretreatment of the selective hydrogenation catalyst, such as subjecting the selective hydrogenation catalyst to pre-sulfurization or carbon monoxide reduction treatments.

Referring again to FIG. 1, in operation, the cracking C4 effluent 112 may be passed to the SHIU 130, where the cracking C4 effluent 112 is contacted with hydrogen in the presence of the selective hydrogenation catalyst to produce the hydrogenation effluent 134. The hydrogen may be provided by hydrogen stream 132, which may be introduced to one or more of the hydrogenation reactors of the SHIU 130 or combined with the cracking C4 effluent 112 upstream of the SHIU 130. Contacting the cracking C4 effluent 112 with hydrogen in the presence of the selective hydrogenation catalyst may cause at least a portion of the 1,3-butadiene from the cracking C4 effluent 112 to undergo hydrogenation reactions to saturate at least one of the carbon-carbon double bonds to form 1-butene. Contact of the cracking C4 effluent with hydrogen in the presence of the selective hydrogenation catalyst may result in a conversion of 1,3-butadiene of at least 90%, at least 95%, at least 98%, at least 99%, or even at least 99.5% by weight. Converting the 1,3-butadiene to normal butenes may increase the yield of propene from the system 100 by providing a greater amount of normal butenes for metathesis to propene and other olefins in the metathesis system downstream of the SHIU 130. The SHIU 130 may be selective for hydrogenating 1,3-butadiene relative to hydrogenation of normal butenes so that the 1,3-butadiene can be hydrogenated to normal butenes without further hydrogenation of the normal butenes produced to n-butane or substantial hydrogenation of the mixed butenes from the cracking C4 effluent 112 to alkanes such as n-butane or isobutane.

Contacting the cracking C4 effluent 112 with hydrogen in the presence of the selective hydrogenation catalyst may also cause isomerization of at least a portion of 1-butene to 2-butenes in the SHIU 130. At least a portion of the 1-butene from the cracking C4 effluent 112, at least a portion of the 1-butene produced through hydrogenation of the 1,3-butadiene, or both may be isomerized to 2-butenes. The degree of hydrogenation of 1,3-butadiene and isomerization of 1-butene to 2-butene may be controlled by controlling the loading of the catalytic metals on the hydrogenation catalyst and by controlling the amount of hydrogen introduced to the SHIU 130 to produce the hydrogenation effluent 134 having a concentration of 2-butene greater than the combined concentrations of 1-butene and isobutene.

The SHIU 130 may be operated at conditions and hydrogen mass flow rate that are sufficient to isomerize 1-butene to 2-butene to the extent that the concentration of 2-butenes in the hydrogenation effluent 134 may be greater than or equal to the sum of the concentration of 1-butene and the concentration of isobutene in the hydrogenation effluent 134. The reaction conditions, mass flow rate of the hydrogen feed, and type of selective hydrogenation catalyst in the SHIU 130 may also reduce or prevent over-hydrogenation of the 1,3-butadiene and mixed butenes to alkanes, such as n-butane.

The cracking C4 effluent 112 may be contacted with hydrogen in the presence of the selective hydrogenation catalyst at a temperature and pressure sufficient to hydrogenate the 1,3-butadiene and isomerize 1-butene to 2-butenes to the extent that the concentration of 2-butene is greater than the combined concentrations of 1-butene and isobutene in the hydrogenation effluent 134. The cracking C4 effluent 112 may be contacted with hydrogen in the presence of the selective hydrogenation catalyst at a temperature of from 50° C. to 100° C., such as from 50° C. to 90° C., from 50° C. to 80° C., from 50° C. to 70° C., from 60° C. to 100° C., from 60° C. to 90° C., from 60° C. to 80° C., from 60° C. to 70° C., from 70° C. to 100° C., from 70° C. to 90° C., or from 70° C. to 80° C. In embodiments, the cracking C4 effluent 112 is contacted with hydrogen in the presence of the selective hydrogenation catalyst at a temperature of from 60° C. to 80° C. The processes of the present disclosure may include controlling a temperature of contacting the cracking C4 effluent 112 with hydrogen in the presence of the selective hydrogenation catalyst in the SHIU 130 in response to the concentration of dienes, such as but not limited to butadiene, in the cracking C4 effluent 112. At greater butadiene concentrations, such as concentrations of butadiene of 40 wt. % or more based on the total weight of the cracking C4 effluent 112, the cracking C4 effluent 112 may be contacted with the hydrogen and selective hydrogenation catalyst at the lesser temperature of 60° C. The temperature of the SHIU 130 may be increased for decreasing concentration of butadiene in the cracking C4 effluent 112 up to the temperature of 80° C. for lesser concentrations of butadiene, such as concentrations less than 20 wt. % or even less than 10 wt. % butadiene based on the total weight of the cracking C4 effluent 112. The cracking C4 effluent 112 may be contacted with hydrogen in the presence of the selective hydrogenation catalyst at a pressure of from 1500 kPa to 2800 kPa, such as from 1500 kPa to 2500 kPa, from 2000 kPa to 2800 kPa, or from 2000 kPa to 2500 kPa. In embodiments, the cracking C4 effluent 112 is contacted with hydrogen in the presence of the selective hydrogenation catalyst at a pressure of from 2000 kPa to 2500 kPa.

The cracking C4 effluent may be contacted with hydrogen in the presence of the selective hydrogenation catalyst at a weight hourly space velocity of the cracking C4 effluent 112 of from 2 per hour to 4 per hour, from 3 per hour to 4 per hour, or about 3.5 per hour. The cracking C4 effluent 112 may be contacted with hydrogen in the presence of the selective hydrogenation catalyst at a mass flow ratio of hydrogen to dienes of from 0.1 to 3, such as from 0.1 to 2, from 0.1 to 1.5, from 0.1 to 1, from 0.5 to 3, from 0.5 to 2, from 0.5 to 1.5, from 1 to 3, from 1 to 2, from 1 to 1.5, from 1.5 to 3, from 1.5 to 2, from 2 to 3, or about 2.2, where the mass flow ratio of hydrogen to dienes is a mass flow rate of hydrogen to the SHIU 130 divided by a product of a weight fraction of dienes in the cracking C4 effluent 112 and a mass flow rate of the cracking C4 effluent 112 to the SHIU 130. The processes of the present disclosure may include controlling the mass flow ratio of hydrogen to dienes in the SHIU 130 in response to changes in the concentration of dienes, such as butadiene, in the cracking C4 effluent 112 to avoid over hydrogenating the cracking C4 effluent 112 and saturating normal olefins in the cracking C4 effluent 112. As the concentration of dienes, such as but not limited to butadiene, increases in the cracking C4 effluent 112, the mass flow ration of hydrogen to dienes can be decreased to avoid over-hydrogenation. For instance, when the concentration of dienes is greater than or equal to 40 wt. % in the cracking C4 effluent 112, the mass flow ratio of hydrogen to dienes can be adjusted into a range of from 1 to 1.5. In contrast, when the concentration of dienes is less than 1 wt. % in the cracking C4 effluent 112, the mass flow ratio of hydrogen to dienes can be adjusted into a range of from 2-3. The mass flow ratio of hydrogen to dienes can be controlled by changing a flow rate of hydrogen to the SHIU 130.

In embodiments, the SHIU 130 can include three reactor stages, such as three hydrogenation reactors, in series. The first two hydrogenation reactors can convert the 1,3-butadiene present in the cracking C4 effluent 112 to 1-butene, cis-2-butene, trans -2-butene, or combinations of these. The first two hydrogenation reactors can include the selective hydrogenation catalyst, such as palladium supported on alumina. The selective hydrogenation catalyst can be the same for the first two hydrogenation reactors. The hydrogen stream 132 can be combined with the cracking C4 effluent 112 upstream of the first hydrogenation reactor of the selective hydrogenation unit 130. The third hydrogenation reactor may also include a selective hydrogenation catalyst, which may be the same as or different from the selective hydrogenation catalyst in the first two hydrogenation reactors.

The hydrogenation effluent 134 may be passed out of the SHIU 130 and passed to the metathesis unit 140. The hydrogenation effluent 134 is passed from the SHIU 130 to the metathesis unit 140 without removing the isobutene from the hydrogenation effluent 134. The hydrogenation effluent 134 can include 1-butene, 2-butenes (trans-2-butene, cis-2-butene, or both), and isobutene. The hydrogenation effluent 134 may additionally include butane, isobutane, trace amounts of unconverted 1,3-butadiene, small amounts of C5+ compounds, excess hydrogen and other light gases from the SHIU 130, or combinations of these. The hydrogenation effluent 134 may comprises less than or equal to 5000 parts per million by weight 1,3-butadiene based on the total weight of the hydrogenation effluent 134.

The hydrogenation effluent 134 may include greater than or equal to 15 wt. %, greater than or equal to 18 wt. %, greater than or equal to 20 wt. %, or even greater than or equal to 25 wt. % isobutene based on the total unit weight of the hydrogenation effluent 134. The hydrogenation effluent 134 may include from 15 wt. % to 50 wt. %, from 15 wt. % to 49 wt. %, from 15 wt. % to 45 wt. %, from 15 wt. % to 40 wt. %, from 15 wt. % to 30 wt. %, from 15 wt. % to 20 wt. %, from 18 wt. % to 49 wt. %, from 18 wt. % to 45 wt. %, from 18 wt. % to 40 wt. %, from 18 wt. % to 30 wt. %, from 18 wt. % to 20 wt. %, from 20 wt. % to 49 wt. %, from 20 wt. % to 45 wt. %, from 20 wt. % to 40 wt. %, from 20 wt. % to 30 wt. %, from 25 wt. % to 49 wt. %, from 25 wt. % to 45 wt. %, from 25 wt. % to 40 wt. %, from 25 wt. % to 30 wt. %, from 30 wt. % to 49 wt. %, from 30 wt. % to 45 wt. %, from 30 wt. % to 40 wt. %, from 40 wt. % to 49 wt. %, from 40 wt. % to 45 wt. %, from 15 wt. % to 25 wt. %, or from 15 wt. % to 20 wt. % isobutene based on the total unit weight of the hydrogenation effluent 134.

The hydrogenation effluent 134 passed to the metathesis unit 140 may include a concentration of 2-butenes sufficient to promote production of propene in the metathesis unit 140 and suppress formation of ethylene in the metathesis unit 140. The hydrogenation effluent 134 passed to the metathesis unit 140 may include from 20 wt. % to 70 wt. %, such as from 20 wt. % to 65 wt. %, from 20 wt. % to 60 wt. %, from 20 wt. % to 50 wt. %, from 20 wt. % to 40 wt. %, from 20 wt. % to 30 wt. %, from 30 wt. % to 70 wt. %, from 30 wt. % to 65 wt. %, from 30 wt. % to 60 wt. %, from 30 wt. % to 50 wt. %, from 30 wt. % to 40 wt. %, from 40 wt. % to 70 wt. %, from 40 wt. % to 65 wt. %, from 40 wt. % to 60 wt. %, from 40 wt. % to 50 wt. %, from 50 wt. % to 70 wt. %, from 50 wt. % to 65 wt. %, from 50 wt. % to 60 wt. %, or from 60 wt. % to 70 wt. % 2-butenes, such as trans-2-butene, cis-2-butene, or both, based on the total weight of the hydrogenation effluent 134.

The hydrogenation effluent 134 passed to the metathesis unit 140 may have a concentration of 1-butene of less than or equal to less than or equal to 40 wt. %, less than or equal to 35 wt. %, less than or equal to 30 wt. %, less than or equal to 25 wt. %, less than or equal to 20 wt. %, or even less than or equal to 10 wt. % based on the total weight of the hydrogenation effluent 134. The hydrogenation effluent 134 may have a concentration of 1-butene of from greater than 0 wt. % to 40 wt. %, from greater than 0 wt. % to 35 wt. %, from greater than 0 wt. % to 30 wt. %, from greater than 0 wt. % to 25 wt. %, from greater than 0 wt. % to 20 wt. %, from greater than 0 wt. % to 10 wt. %, from 0 wt. % to 5 wt. %, from 1 wt. % to 40 wt. %, from 1 wt. % to 35 wt. %, from 1 wt. % to 30 wt. %, from 1 wt. % to 25 wt. %, from 1 wt. % to 20 wt. %, from 1 wt. % to 10 wt. %, from 1 wt. % to 5 wt. %, from 5 wt. % to 40 wt. %, from 5 wt. % to 35 wt. %, from 5 wt. % to 30 wt. %, from 5 wt. % to 25 wt. %, from 5 wt. % to 20 wt. %, from 5 wt. % to 10 wt. %, from 10 wt. % to 40 wt. %, from 10 wt. % to 35 wt. %, from 10 wt. % to 30 wt. %, from 10 wt. % to 25 wt. %, from 10 wt. % to 20 wt. %, from 20 wt. % to 40 wt. %, from 20 wt. % to 35 wt. %, or from 20 wt. % to 30 wt. % based on the total unit weight of the hydrogenation effluent 134.

As previously discussed, the hydrogenation effluent 134 passed to the metathesis unit 140 may have a concentration of 2-butenes greater than or equal to the sum of the concentration of 1-butene and the concentration of isobutene in the hydrogenation effluent 134. The hydrogenation effluent 134 may have a mass ratio of 2-butenes (trans-2-butene, cis-2-butene, or both) to the sum of 1-butene and isobutene of from 1 to 9, from 1 to 4, from 1 to 3, or from 1 to 2, where the mass ratio is the mass of 2-butenes in the hydrogenation effluent 134 divided by the sum of the mass of 1-butene and the mass of isobutene in the hydrogenation effluent 134. When the concentration of 2-butenes is less than the combined concentrations of 1-butene and isobutene, the 2-butenes may be quickly consumed due to the greater reaction rates of the metathesis reaction comprising 2-butenes as a reactant and side reactions comprising the 1-butene and isobutene may take place, which can reduce the selectivity towards propene. The reaction rates of the side reactions of 1-butene and isobutene are also much slower, which may reduce the overall conversion of C4 compounds in the metathesis unit 140 if the 2-butene concentration is less than the combined concentrations of 1-butene and isobutene.

As previously discussed, the hydrogenation effluent 134 may further include other C4 compounds, such as butane and isobutane. The hydrogenation effluent 134 may include from 1 wt. % to 50 wt. % butane and isobutane. The hydrogenation effluent 134 may be substantially free of ethylene. As used in this disclosure, the term "substantially free" of a component means less than 1 wt. % of that component in a particular portion of a catalyst, stream, or reaction zone. As an example, the hydrogenation effluent 134, which is substantially free of ethylene, may have less than 1 wt. % of ethylene based on the total unit weight of the hydrogenation effluent 134.

In many conventional metathesis systems, the metathesis feed is further treated to remove isobutene, in particular when ethylene is passed to the conventional metathesis system as a reactant. Removal of isobutene may be done in conventional metathesis systems to avoid consumption of 1-butene in the cross-metathesis of 1-butene with isobutene, which is unproductive for producing propene. However, in the systems 100 and processes of the present disclosure in which ethylene is not used as a reactant, the isobutene is left in the hydrogenation effluent 134 so that the isobutene is passed to the metathesis unit 140 along with the 1-butene and 2-butenes. Instead of removing the isobutene from the hydrogenation effluent 134, the processes of the present disclosure operate the SHIU 130 to isomerize 1-butene to 2-butenes so that the concentration of 2-butenes is greater than the combined concentrations of 1-butene and isobutene, which may result in promoting propene formation and suppressing ethylene formation in the metathesis unit 140. The hydrogenation effluent 134 may be passed directly from the SHIU 130 to the metathesis unit 140 without removing any isobutene from the hydrogenation effluent 134. Additionally, the cracking C4 effluent 112 may be passed from the hydrocarbon cracking system 106 to the SHIU 130 without removing isobutene from the cracking C4 effluent 112. Thus, no isobutene is removed between the hydrocarbon cracking system 106 and the metathesis unit 140. In other words, the isobutene is not removed from the cracking C4 effluent 112 or the hydrogenation effluent 134 upstream of the metathesis unit 140.

Metathesis System

Referring again to FIG. 1, the system 100 includes the metathesis system disposed downstream of the SHIU 130. The metathesis system may include the metathesis unit 140 and the metathesis effluent separation system 150 disposed downstream of the metathesis unit 140. The metathesis unit 140 may be in fluid communication with the SHIU 130 to pass the hydrogenation effluent 134 from the SHIU 130 to the metathesis unit 140. The hydrogenation effluent 134 may be passed directly from the SHIU 130 to the metathesis unit 140 without being passed through any intervening reactor or separation system.

The metathesis unit 140 may be a dual catalyst metathesis unit 140 that includes a metathesis catalyst and a cracking catalyst downstream of the metathesis catalyst. The metathesis unit 140 may be operable to receive the hydrogenation effluent 134 and contact the hydrogenation effluent 134 with the metathesis catalyst and the cracking catalyst downstream of the metathesis catalyst. Contacting the hydrogenation effluent 134 with the metathesis catalyst may cause at least a portion of the mixed butenes in the hydrogenation effluent 134 to undergo at least a metathesis reaction to produce other olefins, such as but not limited to ethylene, propene, pentene, 2-methyl 2-propene, 2-methyl 2-pentene, 3-hexene, butenes, and other C5+ olefins. Contact of the hydrocarbons in the metathesis unit 140 with the cracking catalyst may cause at least a portion of the C5+ olefins to undergo cracking reactions to produce additional propene, ethylene, or both. The metathesis effluent 146 produced from the metathesis unit 140 may be passed to the metathesis effluent separation system 150, which may be operable to receive the metathesis effluent 146 from the metathesis unit 140 and separate the metathesis effluent 146 into one or a plurality of metathesis effluent streams.

As used throughout the present disclosure, "metathesis" refers to an organic reaction that involves the redistribution of fragments of alkenes by the scission and regeneration of carbon-carbon double bonds. As used throughout the present disclosure, a "metathesis catalyst" may refer to a catalyst that promotes the metathesis reaction of alkenes to form other alkenes. Contact of mixed butenes with a metathesis catalyst may result in conversion 2-butene to 1-butene or conversion to 1-butene to 2-butene through "self-metathesis," which is shown in Chemical Reaction 1 (RXN 1). Self-metathesis of 2-butene to 1-butene and 1-butene to 2-butene by the metathesis catalyst may be an equilibrium reaction as denoted by bi-directional arrows with single heads in RXN 1.

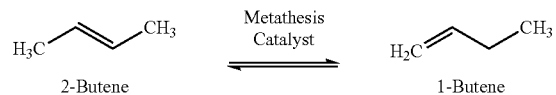

RXN 1

Contact of a mixture of normal butenes (1-butene, trans-2-butene, cis-2-butene, or combinations of these) with the metathesis catalyst may also result in cross-metathesis of 1-butene and 2-butenes. Cross-metathesis between 1-butene and 2-butenes may be achieved with the metathesis catalyst as shown in Chemical Reaction 2 (RXN 2). In the case of cross-metathesis of 2-butenes and 1-butene, the redistribution of these carbon-carbon double bonds through metathesis may produce propene and $C_5$-$C_6$ olefins.

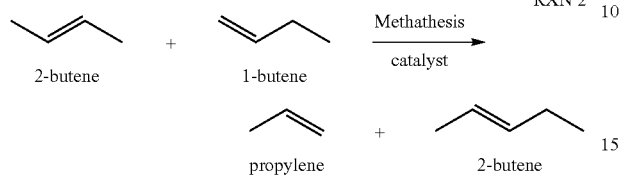

Contact of a mixture of isobutene and normal butenes (1-butene, trans-2-butene, cis-2-butene, or combinations of these) with the metathesis catalyst may also result in cross-metathesis of the isobutene with 2-butenes to produce propene and 2-methyl 2-butene according to the following Chemical Reaction 3 (RXN 3) and cross-metathesis of isobutene with 1-butene to produce ethylene and 2-methyl 2-pentene according to the following Chemical Reaction 4 (RXN 4).

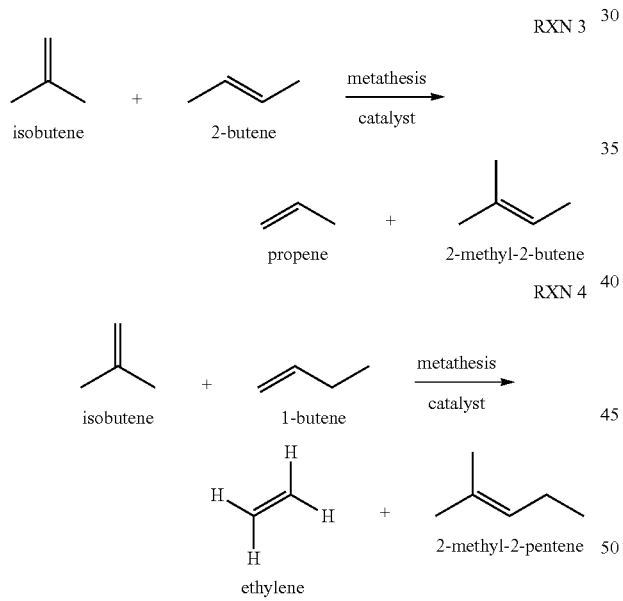

1-Butene can also undergo self-metathesis to produce ethylene and 3-hexene according to the following Chemical Reaction 5 (RXN 5). However, self-metathesis of 2-butene is non-productive, meaning that self-metathesis between two 2-butene molecules produces two 2-butene molecules.

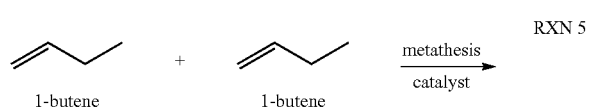

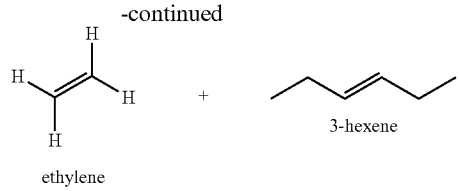

Ethylene produced in RXN 4 and RXN 5 may further undergo cross-metathesis with 2-butene to produce propene according to Chemical Reaction 6 (RXN6).

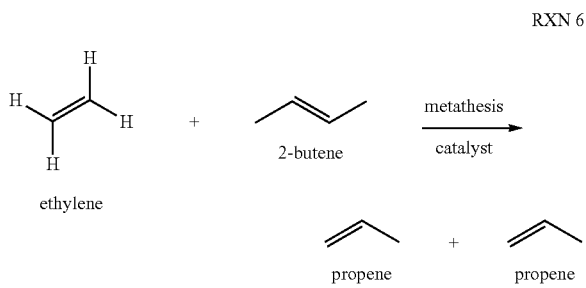

Further, as shown in the following Chemical Reaction 7 (RXN 7), "cracking" refers to the catalytic conversion of $C_4$-$C_6$ alkenes to propene and other alkanes, alkenes, or alkanes and alkenes, for example, $C_1$-$C_2$ alkenes. Catalytic conversion of $C_4$-$C_6$ alkenes to propene and other alkanes, alkenes, or alkanes and alkenes may further increase the yield of propene from the metathesis system.

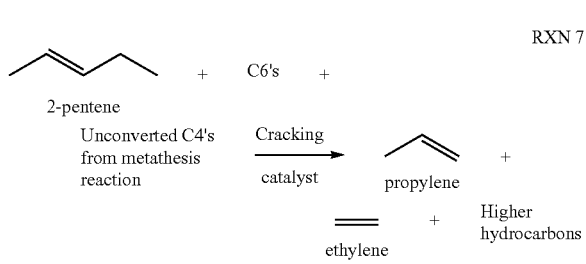

Referring to Chemical Reactions RXN 1-RXN 7, the metathesis and cracking reactions are not limited to these reactants and products; however, Chemical Reactions RXN 1-RXN 7 provide a simplified illustration of the reaction methodology.

As previously discussed, the SHIU 130 is operated so that the hydrogenation effluent 134 fed to the metathesis unit 140 contains isobutene and a concentration of 2-butene that is greater than the sum of the concentrations of 1-butene and isobutene. The presence of isobutene, a greater concentration of 2-butene, and a lesser concentration of 1-butene in the hydrogenation effluent 134 can result in shifting the selectivity of the metathesis unit 140 towards greater production of propene and less production of ethylene. Not intending to be bound by any particular theory, it is believed that the presence of the isobutene and increased concentration of 2-butenes relative to 1-butene in the metathesis unit 140 may promote RXN 2 and RXN 3, which produce propene, and may suppress RXN 4, which produces ethylene and 2-methyl 2-pentene and does not produce propene. It is noted that the reaction rates for RXN 2 and RXN 3 are believed to be much faster compared to the reaction rate for RXN 4. A concentration of 2-butene greater than the combined concentration of 1-butene and isobutene while maintaining isobutene in the hydrogenation effluent 134 may increase the reactant concentrations for RXN 2 and RXN 3 while decreasing the concentration of 1-butene needed for RXN 4. Further, contact of the 2-pentene and 2-methyl 2-butene produced from RXN 2 and RXN 3, respectively, with the cracking catalyst may cause cracking of the 2-pentene and 2-methyl 2-butene to produce additional propene. The excess 2-butene in the hydrogenation effluent 134 may also react with any ethylene produced from RXN 4 and RXN 5 to produce additional propene from RXN 6. Thus, controlling the relative concentrations of metathesis reactants in the hydrogenation effluent 134 passed to the metathesis unit 140 can shift the metathesis unit 140 towards greater propene selectivity.

As previously discussed, the hydrogenation effluent 134, which is passed to the metathesis unit 140 as the metathesis feed, may comprise at least 1-butene, cis-2-butene, trans-2-butene, and isobutene. The hydrogenation effluent may also include other C4 hydrocarbons, such as n-butane, isobutane, or combinations of these. Other compounds may also be present. The hydrogenation effluent 134 may have any of the compositions or properties previously described for the hydrogenation effluent 134. In the processes of the present disclosure, ethylene is not introduced to the metathesis unit 140 as a reactant. In particular, the hydrogenation effluent 134 may be substantially free of ethylene and no external sources of ethylene may be introduced to the metathesis unit 140 or recycled back to the metathesis unit 140. The hydrogenation effluent 134 may have less than 1 wt. % ethylene based on the total weight or mass flow rate of the hydrogenation effluent 134. In embodiments, the hydrogenation effluent 134 passed to the metathesis unit 140 may be substantially free of propene, such as having less than 1 wt. % propene based on the total weight or mass flow rate of the hydrogenation effluent 134. In embodiments, the hydrogenation feed 134 may be substantially free of 1,3-butadiene, such as less than 1.0 wt. % 1,3-butadiene, less than 0.5 wt. % of 1,3-butadiene, or even less than 0.1 wt. % 1,3-butadiene, based on the total weight or mass flow rate of the hydrogenation effluent 134.

Referring again to FIG. 1, the metathesis unit 140 may include one or a plurality of reaction zones, such as but not limited to, a metathesis reaction zone 142, a cracking reaction zone 144, or a combination of both. The metathesis unit 140 may include at least one fixed bed reactor operated in an upflow or a downflow configuration. Although depicted as a fixed bed reactor, the reactors of the metathesis unit 140 may be any other type of reactor suitable for conducting a metathesis reaction. In embodiments, the metathesis unit 140 may include a plurality of metathesis reactors operated in series or in parallel. The metathesis unit 140 may include a plurality of catalyst beds, where each of the catalyst beds may be a separate reaction zone. Two or more of the plurality of catalyst beds or reaction zones may be disposed in a single reactor. In embodiments, metathesis unit 140 may include a single reactor having the metathesis reaction zone 142 comprising the metathesis catalyst and the cracking reaction zone 144 comprising the cracking catalyst, where the cracking reaction zone 144 is disposed downstream of the metathesis reaction zone 142. In embodiments, the cracking catalyst in the cracking reaction zone 144 may be in contact with the metathesis catalyst in the metathesis reaction zone 142.

Figure 4:
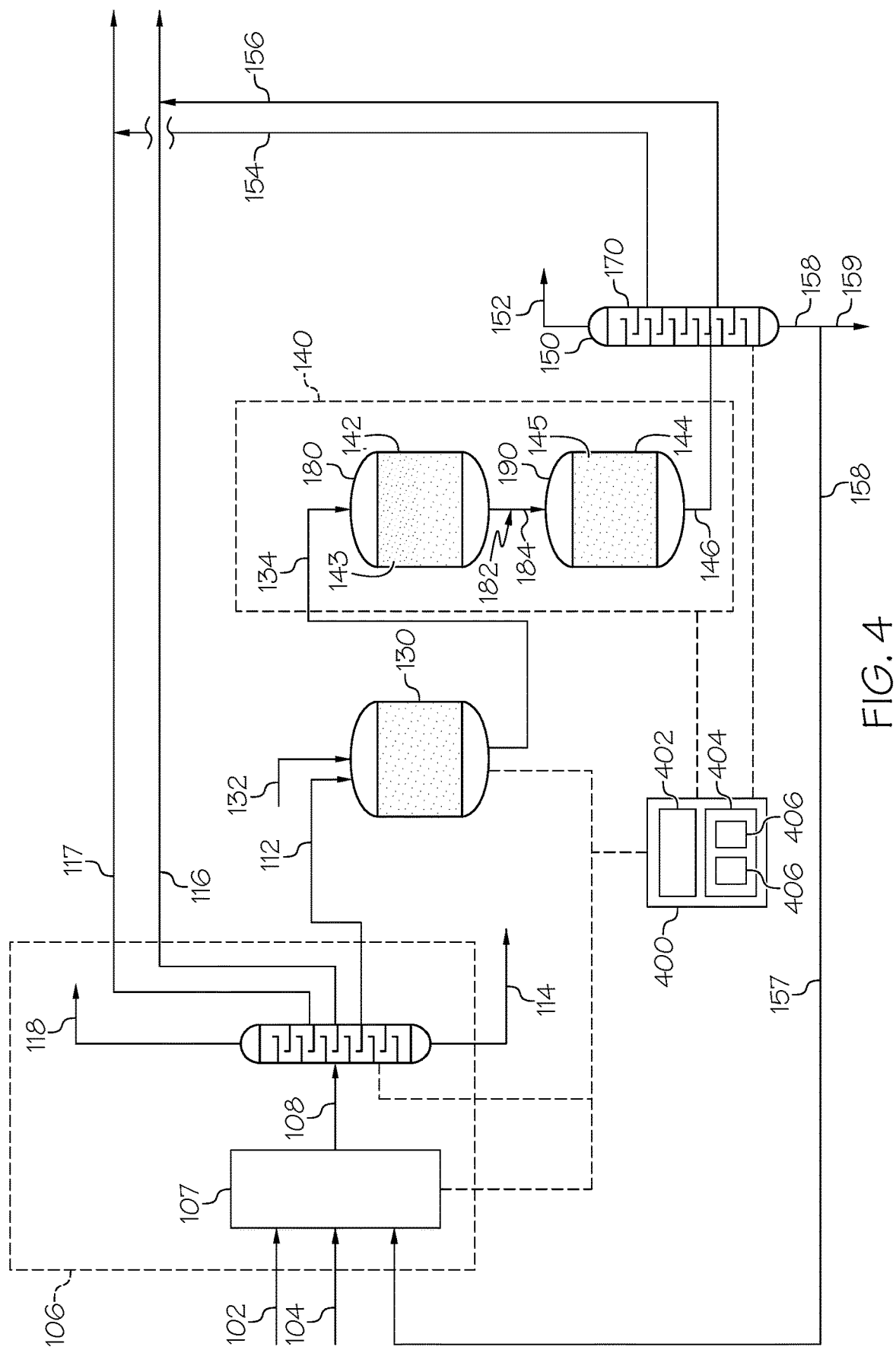
FIG. 4 schematically depicts a generalized flow diagram of another embodiment of a system for producing olefins, according to one or more embodiments shown and described in the present disclosure.
Figure 6:
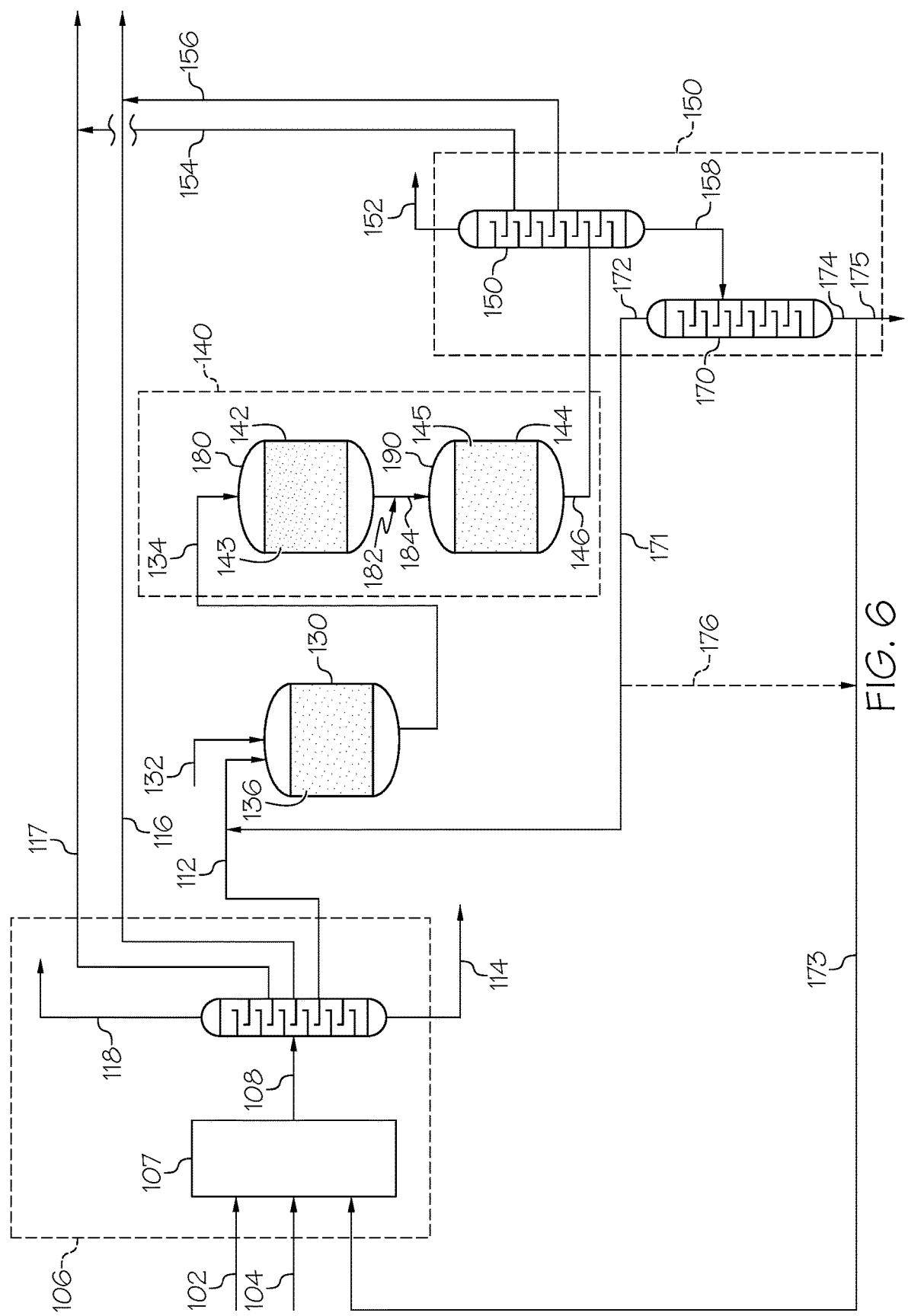
FIG. 6 schematically depicts a generalized flow diagram of still another embodiment of a system for producing olefins, according to one or more embodiments shown and described in the present disclosure.

In embodiments, the metathesis unit 140 may include a plurality of catalyst beds or reaction zones where at least one of the catalyst beds or reaction zones is disposed in a separate reactor from the other of the plurality of catalyst beds or reactions zones. Referring now to FIGS. 4 and 6, the metathesis unit 140 may include a metathesis reactor 180 comprising the metathesis reaction zone 142 having the metathesis catalyst 143 and a cracking reactor 190 disposed directly downstream of the metathesis reactor 180 and comprising the cracking reaction zone 144 that includes the cracking catalyst 145. The metathesis reactor 180 and the cracking reactor 190 may be fluidly coupled by a conduit 182 extending directly from the metathesis reactor 180 to the cracking reactor 190. The conduit 182 may fluidly couple the metathesis reactor 180 to the cracking reactor 190 to pass an effluent 184 from the metathesis reactor 180 directly to the cracking reactor 190 without separation of the effluent 184 from the metathesis reactor 180.

Referring again to FIG. 1, the metathesis unit 140 may be operable to contact the hydrogenation effluent 134 with one or a plurality of catalysts, such as but not limited to the metathesis catalyst, the cracking catalyst, or both. In embodiments, the metathesis unit 140 may include the metathesis reaction zone 142 and the cracking reaction zone 144 downstream of the metathesis reaction zone 142. The metathesis reaction zone 142 may include the metathesis catalyst 143, and the cracking reaction zone 144 may include the cracking catalyst 145. The hydrogenation effluent 134 introduced to the metathesis unit 140 may encounter the metathesis catalyst 143 in the metathesis reaction zone 142 before encountering the cracking catalyst 145 in the cracking reaction zone 144 downstream of the metathesis reaction zone 142.

Contacting of the hydrogenation effluent 134 with the metathesis catalyst 143 may cause at least a portion of the butenes in the hydrogenation effluent 134 to undergo metathesis reactions to produce a metathesis reaction product that includes at least propene. The metathesis catalyst 143 may be any catalyst operable to promote cross-metathesis of butenes to produce propene. The metathesis catalyst may be a particulate catalyst that includes a metal oxide disposed on the surfaces of a catalyst support material. The catalyst support material may be mesoporous silica catalyst support, such as but not limited to one or more molecular sieves or zeolites. As used in the present disclosure, "mesoporous" refers to a material having an average pore size of greater than 2 nanometers and less than 50 nanometers. The mesoporous silica catalyst support may include alumina or may be substantially free of alumina. As a non-limiting example, a mesoporous silica catalyst support that is substantially free of alumina may have less than 1 wt. % alumina.

The metathesis catalyst 143 may include one or a plurality of metal oxides incorporated into the catalyst support material or deposited onto the surfaces of the catalyst support material. The metal oxide may include one or more oxides of a metal from Groups 6-10 of the IUPAC Periodic Table. As non-limiting examples, the metal oxide may include one or more oxides of molybdenum, rhenium, tungsten, or any combination of these. In one or more embodiments, the metal oxide of the metathesis catalyst may be tungsten oxide ($WO_3$). It is contemplated that various amounts of the metal oxide may be impregnated into the mesoporous silica catalyst support. For example and not by way of limitation, the weight percentage (wt. %) of metal oxide, for example $WO_3$, in the metathesis catalyst may be from 1 wt. % to 30 wt. %, such as from 5 wt. % to 25 wt. %, or even from 8 wt. % to 20 wt. % based on the total weight of the metathesis catalyst. The metal oxide may be incorporated into the catalyst support material through co-precipitation, methods, sol-gel methods, or other methods. Alternatively or additionally, the metal oxide may be deposited onto the outer surfaces and pore surfaces of the catalyst support material through any type of impregnation or deposition process, such as but not limited to wet impregnation, vapor deposition, or other suitable method. The amount of metal oxide impregnated onto the catalyst support material of the metathesis catalyst may be verified using inductively coupled plasma (ICP) mass spectrometer or an x-ray fluorescence (XRF) spectrometer to determine the amount of tungsten in a sample of the mesoporous silica catalyst support impregnated with tungsten oxide.

The average pore size of the metathesis catalyst 143 may be obtained from the average surface area and pore size distribution, which are determined using the Brunauer-Emmett-Teller (BET) method according to standard test methods known in the art. Average pore size is generally determined as a pore diameter or pore radius based on the assumption of cylindrical shaped pores. However, it is understood that metathesis catalysts described in this disclosure may have actual shapes that are cylindrical or other shapes, such as, but not limited to, conical, square, slit-shaped, or other irregular shaped pores or combinations of these. The metathesis catalyst may have a relative pore volume per weight of material of at least 0.6 cubic centimeters per gram ($cm^3/g$), such as from 0.6 $cm^3/g$ to 2.5 $cm^3/g$ or even from 0.7 $cm^3/g$ to 1.5 $cm^3/g$. The metathesis catalyst may have a surface area per unit weight of the metathesis catalyst of from 200 meters squared per gram ($m^2/g$) to 600 $m^2/g$, such as from from 225 $m^2/g$ to 350 $m^2/g$, or even from from 250 $m^2/g$ to 325 $m^2/g$. The metathesis catalyst may have a mean particle size of from 20 nanometers (nm) to 200 nm, such as from 50 nm to 150 nm. The metathesis catalyst may have a mean particle size distribution of from 100 angstroms (Å) to 300 A. The mean particle size and mean particle size distribution can be measured using a particle size analyzer, such as a Nanopartica™ series particle size analyzer from Horiba Scientific Company, which measures the size of single particles dispersed in water using ultraviolet (UV) light.

The metathesis catalyst may have a total acidity from 0.001 millimole/gram (mmol/g) to 0.5 mmol/g, from 0.01 mmol/g to 0.5 mmol/g, from 0.1 mmol/g to 0.5 mmol/g, from 0.3 mmol/g to 0.5 mmol/g, from 0.4 mmol/g to 0.5 mmol/g, from 0.001 mmol/g to 4 mmol/g, or from 0.001 mmol/g to 0.3 mmol/g. The acidity of the metathesis catalyst may be generally maintained at or less than 0.5 mmol/g to yield the desired propene selectivity of the multiple-stage catalyst system and to reduce production of undesirable byproducts, such as aromatics.

Referring to FIG. 1, contact of the hydrogenation effluent 134 with the metathesis catalyst in the metathesis reaction zone 142 may produce a metathesis reaction zone product that may include propene and other alkanes and alkenes, such as ethylene, pentene, 2-metyl 2-butene, 2-methyl 2-pentene, 3-hexene, and other C5+ olefins, as previously discussed. The metathesis reaction zone product may also include unreacted mixed butenes, such as cis-2-butene, trans-2-butene, 1-butene, isobutene, or combinations of these. The metathesis catalyst may also promote some self-metathesis of 2-butene to 1-butene, or 1-butene to 2-butene, in the metathesis reaction zone 142.

Referring again to FIG. 1, the metathesis reaction zone product may pass into contact with the cracking catalyst in the cracking reaction zone 144, which may be downstream of the metathesis reaction zone 142. The metathesis reaction zone product stream may be passed directly into contact with the cracking catalyst in the cracking reaction zone 144. The cracking reaction zone 144 may include the cracking catalyst capable of converting at least a portion of the unreacted 2-butene, at least a portion of the C5+ olefins, or both from the metathesis reaction zone product stream, to lighter olefins, such as ethylene and propene.

The cracking catalyst may be any catalyst capable of catalyzing the cracking of C5+ olefins to produce additional propene, ethylene, or both. The cracking catalyst may be a zeolite. In embodiments, the cracking catalyst may be a structured zeolite, such as MFI or BEA structured zeolite, for example. The cracking catalyst may be an MCM-41 catalyst or an SBA-15 catalyst. The cracking catalyst may be an MFI structured silica catalyst. For example, the MFI structured silica-containing catalyst may include MFI structured aluminosilicate zeolite catalysts or MFI structured silica catalysts that do not contain alumina or are substantially free of alumina, such as having less than 0.01 wt. % alumina based on the total weight of the catalyst. The cracking catalyst may be a MFI structured silica-containing catalyst may include other impregnated metal oxides in addition to or as an alternative to alumina. The cracking catalyst may include one or more of the metal oxides of a metal from Groups 6-10 of the IUPAC Periodic Table, more specifically, metal oxides of molybdenum, rhenium, tungsten, titanium, or combinations of these. It should be understood that the cracking catalyst may include a combination of multiple zeolites, such as zeolite particles which include multiple types of zeolites, or a mixture of zeolite particles where particles include different zeolites. The cracking catalyst may be an MFI structured aluminosilicate zeolite catalyst may have a molar ratio of silica to alumina of from 5 to 5000. Various suitable commercial embodiments of cracking catalyst comprising MFI structured aluminosilicate zeolites are contemplated, for example, ZSM-5 zeolites such as MFI-280 produced by Zeolyst International or MFI-2000 produced by Saudi Aramco. Various suitable commercial embodiments are also contemplated for the alumina free MFI structured silica-containing catalysts. One such example is Silicalite-1 produced by Saudi Aramco.

The cracking catalyst may have an average pore size of from 1.5 nm to 3 nm, or from 1.5 nm to 2.5 nm. The cracking catalyst may have an average relative pore volume per weight of material of from 0.1 $cm^3/g$ to 0.3 $cm^3/g$, or from 0.15 $cm^3/g$ to 0.25 $cm^3/g$. The cracking catalyst may have an average surface area of from 300 $m^2/g$ to 425 $m^2/g$, or from 340 $m^2/g$ to 410 $m^2/g$. The cracking catalyst may have an individual crystal size of from 10 microns to 40 microns, from 15 microns to 40 microns, or from 20 microns to 30 microns. The cracking catalyst may have a total acidity of from 0.001 mmol/g to 0.1 mmol/g, or from 0.01 mmol/g to 0.08 mmol/g. The acidity may be maintained at or less than 0.1 mmol/g to reduce production of undesirable byproducts, such as aromatic compounds. Increasing acidity may increase the amount of cracking; however, this increased cracking may also lead to less selectivity and increased production of aromatic hydrocarbon byproducts, which may lead to catalyst coking and deactivation. In some cases, the cracking catalyst may be modified with an acidity modifier to adjust the level of acidity in the cracking catalyst. Examples of acidity modifiers may include, but are not limited to, rare earth modifiers, phosphorus modifiers, potassium modifiers, or combinations of each. Alternatively, the cracking catalysts may be substantially free of acidity modifiers, such as those selected from rare earth modifiers, phosphorus modifiers, potassium modifiers, or combinations of each.

Referring again to FIG. 1, the hydrogenation effluent 134 may be contacted with the metathesis catalyst and cracking catalyst in the metathesis unit 140 under conditions sufficient to promote the cross-metathesis of at least a portion of the mixed butenes in the hydrogenation effluent 134 to produce propene. The hydrogenation effluent 134 may be contacted with the metathesis catalyst and cracking catalyst at a gas hourly space velocity (GHSV) of from 10 per hour ($h^{-1}$) to 10,000 $h^{-1}$, such as from 100 $h^{-1}$ to 5000 $h^{-1}$, or from 300 $h^{-1}$ to 2500 $h^{-1}$. The hydrogenation effluent 134 may be contacted with the metathesis catalyst and cracking catalyst in the metathesis unit 140 at a temperature of from 200° C. to 600° C., such as from 300° C. to 550° C., or even from 350° C. to 500° C. The hydrogenation effluent 134 may be contacted with the metathesis catalyst and cracking catalyst in the metathesis unit 140 at a pressure of from 1 bar (100 kPa) to 30 bar (3,000 kPa) or from 2 bar (200 kPa) to 20 bar (2,000 kPa). In embodiments, the hydrogenation feed 134 may be contacted with the metathesis catalyst and cracking catalyst in the metathesis unit 140 at atmospheric pressure.

Contact of the hydrogenation effluent 134 with the metathesis catalyst and cracking catalyst in the metathesis unit 140 under reaction conditions may produce a metathesis effluent 146 comprising propene and other olefins. The metathesis effluent 146 may be passed out of the metathesis unit 140. The metathesis effluent 146 may additionally include one or more of ethylene, unreacted butenes, fuel gas, propane, isobutane, n-butane, isobutene, butadiene, and C5+ compounds. At least a portion of the propane, n-butane, isobutane, and butadiene in the metathesis effluent 146 may be constituents that pass through the metathesis unit 140 without undergoing reaction to form olefins. The ethylene and certain C5+ compounds, such as but not limited to pentene, 2-methyl 2-butene, 2-methyl 2-pentene, 3-hexene, and combinations of these may be produced in the metathesis unit 140 by the metathesis reactions. At least a portion of the C5+ olefins may be converted to propene, ethylene, or other compounds through contact with the cracking catalyst in the metathesis unit 140.

Referring to FIGS. 1 and 4, the metathesis effluent 146 may be passed from the metathesis unit 140 to the metathesis effluent separation system 150. The metathesis effluent separation system 150 may be in fluid communication with the metathesis unit 140 so that the metathesis effluent 146 can be passed directly from the metathesis unit 140 to the metathesis effluent separation system 150 without passing through any intervening unit operations, such as reactors. The metathesis effluent separation system 150 may include one or a plurality of separators operable to separate the metathesis effluent 146 into a plurality of olefin containing effluents, such as at least a metathesis propene effluent 156 and a metathesis C4+ effluent 158. The metathesis effluent separation system 150 may be operable to separate the metathesis effluent 146 into metathesis light gases 152, a metathesis ethylene effluent 154, the metathesis propene effluent 156, the metathesis C4+ effluent 158, or combinations of these. The separators/separation units of the metathesis effluent separation system 150 may include, but are not limited to, flash drums, high-pressure separators, distillation units, fractional distillation units, membrane separation units, or combinations of these.

The metathesis propene effluent 156 may include the propene from the metathesis reaction effluent 146. The metathesis propene effluent 156 may include at least 90%, at least 95%, at least 98%, at least 99%, or at least 99.5% of the propene from the metathesis reaction effluent 146. The metathesis ethylene effluent 154 may include the ethylene from the metathesis reaction effluent 146. The metathesis ethylene effluent 154 may include at least 90%, at least 95%, at least 98%, at least 99%, or at least 99.5% of the ethylene from the metathesis reaction effluent 146. The metathesis propene effluent 156 and the metathesis ethylene effluent 154 may be passed to one or more downstream unit operations for further processing, such as but not limited to purification or polymerization processes. The metathesis propene effluent 156 may be combined with the cracking propene effluent 116 from the hydrocarbon cracking system 106 to form a combined propene effluent from the system 100. Likewise, the metathesis ethylene effluent 154 may be combined with the cracking ethylene effluent 117 from the hydrocarbon cracking system 106 to form a combined ethylene effluent from the system 100. The combined propene effluent and the combined ethylene effluent from the system 100 may be passed independently to downstream operations for further processing. The metathesis light gases 152 may include excess hydrogen, methane, and other light gases present in the metathesis reaction effluent 154 and having boiling point temperatures less than ethylene. The metathesis light gases 152 may be passed to one or more downstream treatment systems for further processing, such as recovery of hydrogen or removal of contaminants such as sulfur and nitrogen containing gases. Excess hydrogen recovered from the metathesis light gases 152 may be recycled back to the SHIU 130 as a portion of the hydrogen stream 132.

In embodiments, the metathesis ethylene effluent 154 may not be passed back to the metathesis unit 140 and no supplemental ethylene may be introduced or passed to the metathesis unit 140. Ethylene itself can be a valuable intermediate for producing other chemical products, such as polyethylene and other polymers. Thus, the metathesis unit 140 may be operated in the absence of any supplemental ethylene introduced to the metathesis unit 140 and the only ethylene present in the metathesis unit 140 may be any trace amounts of ethylene incidentally present in the hydrogenation effluent 134 passed to the metathesis unit 140 and any ethylene produced in the metathesis reactor 140, such as through metathesis of 1-butene with itself according to RXN 5 or with isobutene according to RXN 4.

Referring again to FIGS. 1 and 4, the metathesis C4+ effluent 158 may include constituents from the metathesis reaction effluent 146 having at least four carbon atoms. The metathesis C4+ effluent 158 may include at least 90%, at least 95%, at least 98%, at least 99%, or even at least 99.5% by weight of the constituents of the metathesis reaction effluent 146 having at least four carbon atoms. The metathesis C4+ effluent 158 may include unreacted mixed butenes, n-butane, isobutane, 1,3-butadiene, 2-methyl 2-butene, pentenes, 2-methyl 2-pentene, 3-hexene, and any other C5+ alkanes or olefins produced in or carried through the metathesis unit 140. The metathesis C4+ effluent 158 may be recycled back to the hydrocarbon cracking system 106 through metathesis C4+ recycle line 157. The metathesis C4+ effluent 158 may be passed directly to the hydrocarbon cracking unit 107 of the hydrocarbon cracking system 106 or combined with the hydrocarbon feed 102 upstream of the hydrocarbon cracking unit 107. Constituents of the metathesis C4+ effluent 158 may be cracked along with the hydrocarbon feed 102 in the hydrocarbon cracking system 106 to produce additional olefins, such as ethylene, propene, and mixed butenes, thereby increasing the yield of light olefins, in particular pentene, from the system 100. At least a portion of the metathesis C4+ effluent 158 may be passed out of the system 100 through metathesis C4+ bleed line 159, which may prevent buildup of non-reactive compounds and contaminants in the system 100.

Figure 5:
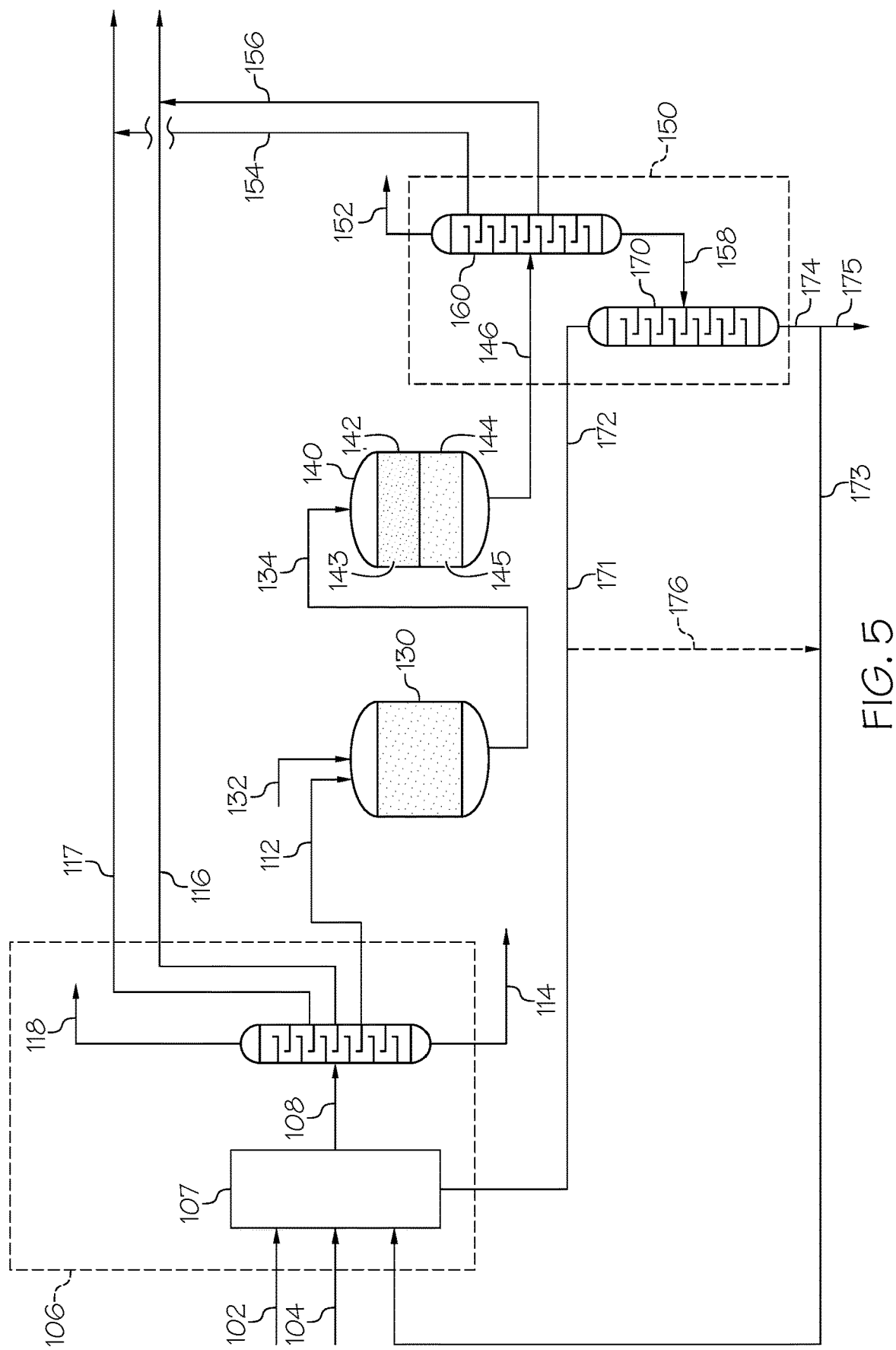
FIG. 5 schematically depicts a generalized flow diagram of another embodiment of a system for producing olefins, according to one or more embodiments shown and described in the present disclosure.

Referring now to FIG. 5, the metathesis effluent separation system 150 may be further operable to separate the metathesis C4+ effluent 158 to produce a metathesis C4 effluent 172 and a metathesis C5+ effluent. The metathesis effluent separation system 150 may include a first separator 160 operable to separate the metathesis reaction effluent 146 to produce the metathesis light gases 152, the metathesis ethylene effluent 154, the metathesis propene effluent 156, and the metathesis C4+ effluent 158. The metathesis effluent separation system 150 may further include a second separation unit 170 downstream of the first separation unit 160. The second separation unit 170 may be operable to separate the metathesis C4+ effluent 158 to produce the metathesis C4 effluent 172 and the metathesis C5+ effluent 174.

The metathesis C4 effluent 172 may include constituents of the metathesis reaction effluent 146 having four carbon atoms, such as but not limited to unreacted mixed butenes, butane, isobutane, and 1,3-butadiene. The metathesis C4 effluent 172 may include at least 90%, at least 95%, at least 98%, at least 99%, or even at least 99.5% by weight of the constituents of the metathesis reaction effluent 146 having four carbon atoms. The metathesis C4 effluent 172 may be passed back to the SHUI 130 through metathesis C4 recycle line 171. In the SHIU 130, the 1,3-butadiene from the metathesis C4 effluent 172 may undergo hydrogenation to produce 1-butene and at least a portion of the 1-butene from the metathesis C4 effluent 172 may undergo isomerization to 2-butene through contact with hydrogen in the presence of the selective hydrogenation catalyst at the reaction conditions in the SHIU 130. Passing the metathesis C4 effluent 172 back to the SHIU 130 may further increase the conversion of butenes and increase the yield of propene from the system 100.

The metathesis C5+ effluent 174 may include the constituents from the metathesis reaction effluent 146 having at least five carbon atoms. The metathesis C5+ effluent 174 may include at least 90%, at least 95%, at least 98%, at least 99%, or even at least 99.5% by weight of the constituents of the metathesis reaction effluent 146 having at least five carbon atoms. The metathesis C5+ effluent 174 may include but is not limited to 2-methyl 2-butene, pentenes, 2-methyl 2-pentene, 3-hexene, and any other C5+ alkanes or olefins produced in or carried through the metathesis unit 140. The metathesis C5+ effluent 174 may be passed back to the hydrocarbon cracking system 106 through metathesis C5+ recycle line 173. The metathesis C5+ effluent 174 may be passed directly to the hydrocarbon cracking unit 107 of the hydrocarbon cracking system 106 or combined with the hydrocarbon feed 102 upstream of the hydrocarbon cracking unit 107. Constituents of the metathesis C5+ effluent 174 may be cracked along with the hydrocarbon feed 102 in the hydrocarbon cracking system 106 to produce additional olefins, such as ethylene, propene, and mixed butenes, thereby increasing the yield of light olefins, in particular propene, from the system 100. The system 100 may include a metathesis C5+ recycle line 173 that may be operable to pass the metathesis C5+ effluent 174 from the metathesis effluent separation system 150 back to the hydrocarbon cracking system 106. At least a portion of the metathesis C5+ effluent 174 may be passed out of the system 100 through metathesis C5+ bleed line 175, which may prevent build-up of non-reactive compounds and contaminants in the system 100.

In embodiments, at least a portion of the metathesis C4 effluent 172 may be combined with the metathesis C5+ effluent 174 and passed back to the hydrocarbon cracking system 106. The portion of the metathesis C4 effluent 172 may be passed into contact with the metathesis C5+ effluent 174 through line 176 in FIG. 5.

Referring now to FIG. 6, an embodiment of the system 100 is schematically depicted in which the metathesis unit 140 comprises the metathesis reactor 180 and the separate cracking reactor 190 disposed downstream of the metathesis reactor 180. The metathesis reaction zone 142 comprising the metathesis catalyst 143 is disposed in the metathesis reactor 180, and the cracking reaction zone 144 comprising the cracking catalyst 145 is disposed in the cracking reactor 190. A direct conduit 182 extends directly between the metathesis reactor 180 and the cracking reactor 190 to pass the effluent 184 from the metathesis reactor 180 directly to the cracking reactor 190 without separation of the effluent 184.

The system 100 depicted in FIG. 6 further comprises the metathesis effluent separation system 150 that includes the first separator 160 and the second separator 170 downstream of the first separator 160. The first separator 160 may be operable to separate the metathesis reaction effluent 146 to produce the metathesis light gases 152, the metathesis ethylene effluent 154, the metathesis propene effluent 156, and the metathesis C4+ effluent 158, and the second separation unit 170 may be operable to separate the metathesis C4+ effluent 158 to produce the metathesis C4 effluent 172 and the metathesis C5+ effluent 174, as previously discussed. The metathesis C4 effluent 172 may be passed back to the SHIU 130, and the metathesis C5+ effluent 174 may be passed back to the hydrocarbon cracking system 106.

Figure 7:
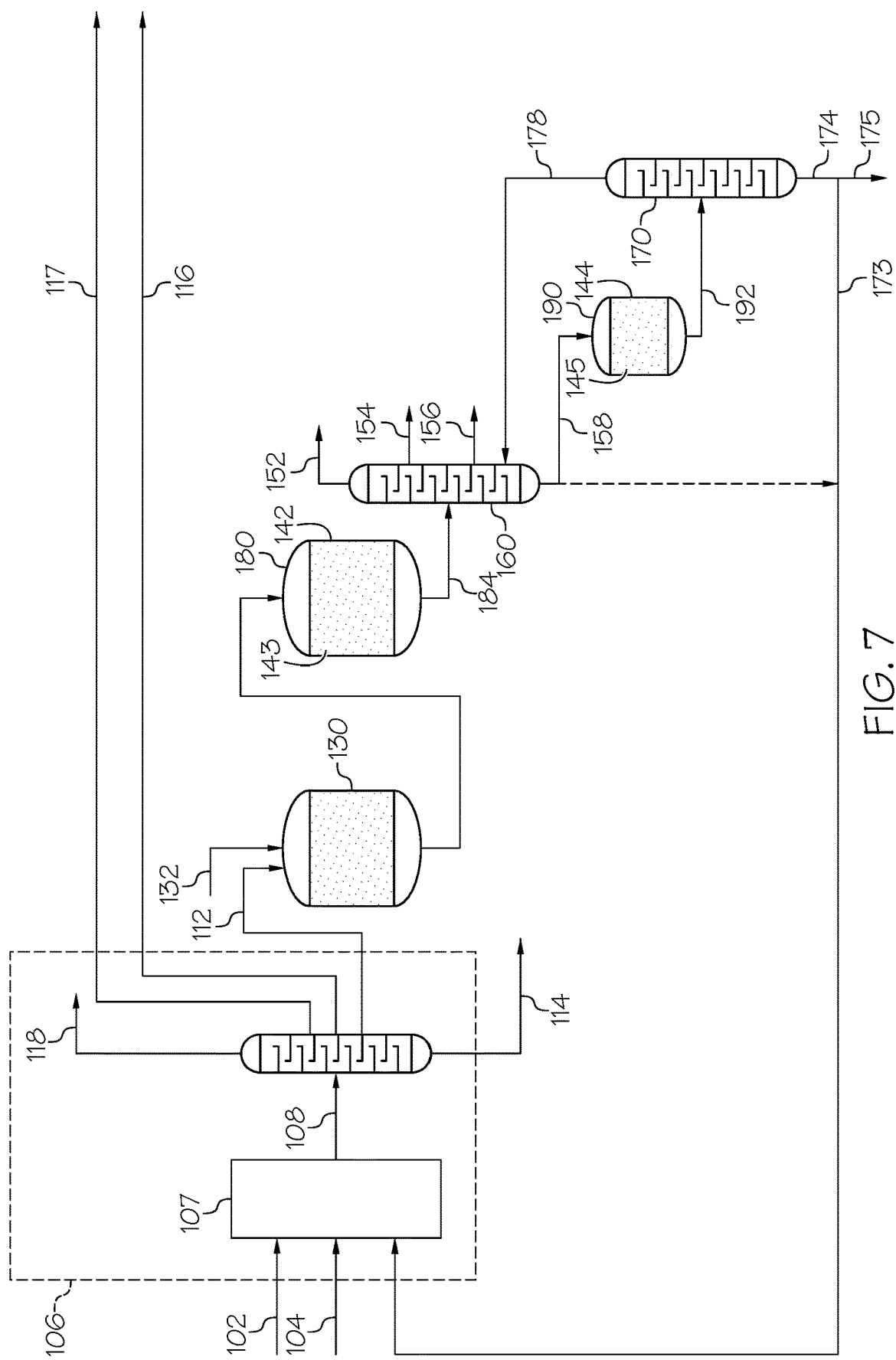
FIG. 7 schematically depicts a generalized flow diagram of another embodiment of a system for producing olefins, according to one or more embodiments shown and described in the present disclosure.

Referring now to FIG. 7, in an embodiment, the system 100 may include the metathesis reactor 180 and the cracking reactor 190 downstream of the metathesis reactor 180. The metathesis reactor 180 may include the metathesis reaction zone 142 comprising the metathesis catalyst 143. The metathesis reactor 180 may be operable to contact the hydrogenation effluent 134 with the metathesis catalyst 143 to produce the effluent 184 comprising metathesis reaction products and unconverted reactants. In the embodiment of system 100 depicted in FIG. 7, the effluent 184 from the metathesis reactor 160 may be passed to the first separation unit 160, which may be operable to separate the effluent 184 from the metathesis reactor 180 into the light gases 152, the metathesis ethylene effluent 154, the metathesis propene effluent 156, and a metathesis C4+ effluent 158. The metathesis C4+ effluent 158 may then be passed to the cracking reactor 190, which may be operable to contact the metathesis C4+ effluent 158 with the cracking catalyst 145 in the cracking reaction zone 144 to produce a cracking reactor effluent 192.

The cracking reactor effluent 192 may be passed to the second separator 170, which may be operable to separate the cracking reactor effluent 192 to produce a C4-stream 178 and the metathesis C5+ effluent 174. The C4-stream 178 may include constituents of the cracking reactor effluent 192 having less than or equal to 4 carbon atoms. The C4-stream 178 may be passed from the second separator 170 back to the first separator 160. The first separator 160 may separate the C4-stream 178 along with the effluent 184 from the metathesis reactor 180 to produce the light gases 152, the metathesis ethylene effluent 154, the metathesis propene effluent 156, and the metathesis C4+ effluent 158.

The metathesis C5+ effluent 174 may include constituents of the cracking reactor effluent 192 having greater than or equal to 5 carbon atoms. The metathesis C5+ effluent 174 may be passed back to the hydrocarbon cracking system 106 through metathesis C5+ recycle line 173. At least a portion of the metathesis C5+ effluent 174 may be passed out of the system 100 through bleed line 175. At least a portion of the metathesis C4+ effluent 158 from the first separator 160 may be bypassed around the cracking reactor 190 to be combined with the metathesis C5+ effluent 174 passed back to the hydrocarbon cracking unit 106.

Control System

Referring again to FIG. 1, in embodiments, the system 100 may include a control system 400 communicatively coupled to the hydrocarbon cracking unit 107, the cracker effluent separation system 110, the SHIU 130, the metathesis unit 140, or combinations of these through one or more wired or wireless communication methods. The control system 400 may include one or a plurality of processors 402, one or a plurality of memory modules 404 communicatively coupled to the processors 402, and machine readable and executable instructions 406 stored on the memory module(s) 404. The machine readable and executable instructions 406, when executed by the at least one processor 402, may cause the control system 400 to automatically operate the hydrocarbon cracking unit 107 to thermally or catalytically crack at least a portion of a hydrocarbon feed 102 to produce a cracker effluent 108 comprising olefins; operate the cracker effluent separation system 110 to separate the cracker effluent 108 to produce at least a cracking C4 effluent 112 comprising at least 1-butene, isobutene, and 1,3-butadiene; operate the SHIU 130 to contact the cracking C4 effluent 112 with hydrogen 132 in the presence of the selective hydrogenation catalyst to produce a hydrogenation effluent 134; and operate the metathesis unit 140 to contact the hydrogenation effluent 134 with the metathesis catalyst and cracking catalyst to produce a metathesis reaction effluent 146 comprising at least propene. The machine readable and executable instructions 406, when executed by the at least one processor 402, may also cause the control system 400 to automatically maintain the SHIU 130 under operating conditions sufficient to convert the 1,3-butadiene to 1-butene and isomerize 1-butene to 2-butene so that a concentration of 2-butenes in the hydrogenation effluent 134 is greater than or equal to a sum of a concentration of 1-butene and a concentration of isobutene in the hydrogenation effluent 134.

The hydrocarbon cracking unit 107, the cracker effluent separation system 110, the SHIU 130, and the metathesis unit 140 may have any of the features, configurations, and operating conditions previously described for these unit operations. The selective hydrogenation catalyst may comprise, consist of, or consist essentially of from 0.3 weight percent to 0.5 weight percent transition metal, such as palladium, supported on an alumina catalyst support. The selective hydrogenation catalyst may have any of the other features previously described for the selective hydrogenation catalyst. The machine readable and executable instructions 406, when executed by the at least one processor 402, may cause the control system 400 to automatically operate the SHIU 130 at a temperature of from 60° C. to 80° C., a pressure of from 2,000 kPa to 2,500 kPa, a weight hourly space velocity of the cracking C4 effluent 112 of from 2 per hour to 4 per hour or about 3.5 per hour, a mass flow ratio of hydrogen to diene of 2.2, or combinations of these reaction conditions. The control system 400 may operate the SHIU 130 at any of the other conditions previously discussed for the SHIU 130.

The hydrocarbon cracking unit 107 may be a high-severity fluidized catalytic cracking unit 200 (FIG. 2) communicatively coupled to the control system 400, and the machine readable and executable instructions 406, when executed by the at least one processor 402, may cause the control system 400 to automatically operate the high-severity fluidized catalytic cracking unit 200 to contact the hydrocarbon feed 102 with a cracking catalyst under high-severity conditions, where the high-severity conditions may comprise a temperature of greater than or equal to 500° C., a residence time of less than 3 seconds, a cracking catalyst to hydrocarbon weight ratio of greater than 5:1, or combinations of these conditions. In embodiments, the hydrocarbon cracking unit 107 may be a steam cracking unit 300 (FIG. 3) communicatively coupled to the control system 400, and the machine readable and executable instructions 406, when executed by the at least one processor 402, may cause the control system 400 to automatically operate the steam cracking unit 300 to contact the hydrocarbon feed 102 with steam 104 at a temperature of from 700° C. to 900 ° C. The machine readable and executable instructions 406, when executed, may cause the control system 400 to operate the high-severity fluid catalytic cracking unit 200 or steam cracking unit 300 at any of the conditions previously described in the present disclosure for these units.

Referring again to FIG. 1, in embodiments, the system 100 may include the metathesis effluent separation system 150 disposed downstream of the metathesis unit 140 and communicatively coupled to the control system 400. The machine readable and executable instructions 406, when executed by the at least one processor 402, may cause the control system 400 to automatically operate the metathesis effluent separation system 150 to separate the metathesis reaction effluent 146 into at least a metathesis propene effluent 156 and a metathesis C4+ effluent 158 and pass at least a portion of the metathesis C4+ effluent 158 back to the hydrocarbon cracking unit 107. The system 100 may include the metathesis C4+ recycle line 157 fluidly coupling the metathesis effluent separation system 150 to the hydrocarbon cracking unit 107 for passing at least a portion of the metathesis C4+ effluent 158 back to the hydrocarbon cracking unit 107. The metathesis effluent separation system 150 may have any of the features previously described for this unit. In embodiments, the metathesis effluent separation system 150 may include a plurality of separation units. The machine readable and executable instructions 406, when executed by the at least one processor 402, may cause the control system 402 to automatically operate the metathesis effluent separation system 150 to further separate the metathesis C4+ effluent 158 into a metathesis C4 effluent 172 and a metathesis C5+ effluent 174, pass at least a portion of the metathesis C5+ effluent 174 to the hydrocarbon cracking unit 107, and pass at least a portion of the metathesis C4 effluent 172 to the SHIU 130.

Referring again to FIG. 1, the metathesis unit 140 of the metathesis system may be in direct fluid communication with the SHIU 130 so that the hydrogenation effluent 134 can be passed directly from the SHIU 130 to the metathesis unit 140 of the metathesis system. In embodiments, the metathesis catalyst and the cracking catalyst may be disposed in a single reactor, as shown in FIG. 1, so that the hydrogenation effluent 134 passed to the metathesis unit 140 contacts the metathesis catalyst and then the cracking catalyst directly after contacting the metathesis catalyst. Referring again to FIG. 4, the metathesis catalyst may be disposed in a metathesis reactor 180 and the cracking catalyst may be disposed in a cracking reactor 190 separate from and disposed downstream of the metathesis reactor 180. The cracking reactor 190 may be directly downstream of the metathesis reactor 180 and the conduit 182 may extend directly between the metathesis reactor 180 and the cracking reactor 190 so that the effluent 184 from the metathesis reactor 180 can be passed directly to the cracking reactor 190. In embodiments, the system 100 does not include a supplemental ethylene feed to the metathesis unit 140.

The control system 400 described in the present disclosure is an example of a suitable computing device but do not suggest any limitation on the scope of any embodiments presented. Nothing illustrated or described with respect to the control system 400 should be interpreted as being required or as creating any type of dependency with respect to any element or plurality of elements of the present disclosure. It is understood that various methods and control schemes described in the present disclosure may be implemented using one or more analog control devices in addition to or as an alternative to the control system 400. The control system 400 may include, but is not limited to, an industrial controller, desktop computer, laptop computer, server, client computer, tablet, smartphone, or any other type of device that can send data, receive data, store data, and perform one or more calculations. The control system 400 can include a display. The control system 400 may further include one or more input devices which can include, by way of example, any type of mouse, keyboard, keypad, push button array, switches, disk or media drive, memory stick (thumb drive), memory card, pen, touch-input device, biometric scanner, audio input device, sensors, or combinations of these. In embodiments, the input devices may include a plurality of the sensors (not shown), such as temperature sensors, pressure sensors, flowrate sensors, composition sensors, or other sensors, positioned at various points in the system 100. The control system 400 communicatively coupled to the hydrocarbon cracking unit 107, the cracker effluent separation system 110, the SHIU 130, the metathesis unit 140, and the metathesis effluent separation system 150 is intended to include communicatively coupling the control system 400 to output devices associated with each of these process units, where the output devices can include but are not limited to the various pumps, valves, heat exchangers, compressors, or other output devices associated with operation of each of the process units of the system 100. It is understood that operating a process unit, such as the SHIU 130, refers to operating all the various output control devices associated with that process unit.

Any of the memory modules described in the present disclosure may include a non-volatile memory (ROM, flash memory, etc.), volatile memory (RAM, etc.), or a combination of these. The control system 400 of the present disclosure can include a network interface device, which can facilitate communication with the input devices and output devices or over a network via wires, via a wide area network, via a local area network, via a personal area network, via a cellular network, via a satellite network, or a combination of these. Suitable local area networks may include wired Ethernet and/or wireless technologies such as, for example, wireless fidelity (Wi-Fi). Suitable personal area networks may include wireless technologies such as, for example, IrDA, Bluetooth, Wireless USB, Z-Wave, ZigBee, other near field communication protocols, or combinations of these. Suitable personal area networks may similarly include wired computer buses such as, for example, USB and FireWire. Suitable cellular networks include, but are not limited to, technologies such as LTE, WiMAX, UMTS, CDMA, and GSM. Network interface 173 can be communicatively coupled to any device capable of transmitting data, receiving data, or both via a network.

The hardware of the network interface devices can include a communication transceiver for sending, receiving, or both, any wired or wireless communication. Various components, such as valves, pumps, heat exchangers, compressors, sensors, or combinations of these may utilize one or more network interface devices to communicate with the control system 400 through the network. For example, the hardware of the network interface devices may include an antenna, a modem, LAN port, Wi-Fi card, WiMax card, mobile communications hardware, near-field communication hardware, satellite communication hardware and/or any wired or wireless hardware for communicating with other networks and/or devices.

The one or more memory modules described in the present disclosure may include one or a plurality of computer readable storage mediums, each of which may be either a computer readable storage medium or a computer readable signal medium. A computer readable storage medium may reside, for example, within an input device, non-volatile memory, volatile memory, or any combination thereof. A computer readable storage medium can include tangible media that is able to store instructions associated with, or used by, a device or system. A computer readable storage medium includes, by way of non-limiting examples: RAM, ROM, cache, fiber optics, EPROM/Flash memory, CD/DVD/BD-ROM, hard disk drives, solid-state storage, optical or magnetic storage devices, diskettes, electrical connections having a wire, or any combination thereof. A computer readable storage medium may also include, for example, a system or device that is of a magnetic, optical, semiconductor, or electronic type. Computer readable storage media and computer readable signal media are mutually exclusive.

A computer readable signal medium can include any type of computer readable medium that is not a computer readable storage medium and may include, for example, propagated signals taking any number of forms such as optical, electromagnetic, or a combination thereof. A computer readable signal medium may include propagated data signals containing computer readable code, for example, within a carrier wave.

The depictions of the control system 400 in the drawings are simplified representations of the control system 400. Many components of the computing controllers have been omitted for purposes of clarity. Assembling various hardware components into a functioning controller of computing device is considered to be part of the ordinary skill in the art. It is noted that recitations herein of a component of the present disclosure being "configured," "structured," or "programmed" in a particular way, to embody a particular property, or to function in a particular manner, are structural recitations, as opposed to recitations of intended use. More specifically, the references herein to the manner in which a component is "configured," "structured," or "programmed" denotes an existing physical condition of the component and, as such, is to be taken as a definite recitation of the structural characteristics of the component.

Referring again to FIG. 1, the present disclosure also includes processes for producing olefins. The processes may include passing the hydrocarbon feed 102 to the hydrocarbon cracking unit 107 that may crack at least a portion of the hydrocarbon feed 102 to produce the cracker effluent 108 and passing the cracker effluent 108 to the cracker effluent separation system 110 that may separate the cracker effluent 108 to produce at least the cracking C4 effluent 112 that comprises at least 1-butene, 1,3-butadiene, and isobutene. The processes further include passing the cracking C4 effluent 112 to the SHIU 130 that contacts the cracking C4 effluent 112 with hydrogen 132 in the presence of a selective hydrogenation catalyst to produce the hydrogenation effluent 134. Contacting the cracking C4 effluent 112 with the hydrogen 132 in the presence of the selective hydrogenation catalyst hydrogenates 1,3-butadiene to 1-butene, n-butane, or both and isomerizes at least a portion of the 1-butene to 2-butenes so that the concentration of 2-butenes in the hydrogenation effluent 134 is greater than or equal to the sum of the concentration of 1-butene and the concentration of isobutene in the hydrogenation effluent 134. The processes may further include passing the hydrogenation effluent 134 to the metathesis unit 140 that contacts the hydrogenation effluent 134 with the metathesis catalyst and the cracking catalyst downstream of the metathesis catalyst to produce the metathesis reaction effluent 146 comprising at least propene. Contacting the hydrogenation effluent 134 with the metathesis catalyst may cause metathesis of at least a portion of the 1-butene, 2-butenes, and isobutene in the hydrogenation effluent 134 to produce a metathesis reaction product comprising at least propene, and contacting with the cracking catalyst may cause at least a portion of C5+ olefins produced through metathesis to undergo cracking reactions to produce propene, ethylene, or both. The concentration of 2-butenes in the hydrogenation effluent 134 being greater than or equal to the sum of the concentration of 1-butene and the concentration of isobutene in the hydrogenation effluent 134 may promote formation of propene and suppress formation of ethylene in the metathesis unit 140. The hydrocarbon cracking unit 107, cracking effluent separation system 110, SHIU 130, and metathesis unit 140 may have any of the features or operating conditions previously discussed for these units.

The hydrogenation effluent 134 may have from 15 wt. % to 50 wt. % isobutene per unit weight of the hydrogenation effluent 134. The hydrogenation effluent 134 may have a mass ratio of 2-butenes to a sum of isobutene and 1-butene of from 1:1 to 9:1, from 1:1 to 4:1, from 1:1 to 3:1, or from 1:1 to 2:1. The selective hydrogenation catalyst may have any of the features previously described for this catalyst. In embodiments, the selective hydrogenation catalyst may comprise, consist of, or consist essentially of a transition metal supported on an alumina catalyst support. In embodiments, the transition metal of the selective hydrogenation catalyst may comprise, consist of, or consist essentially of palladium. In embodiments, the selective hydrogenation catalyst comprises, consists of, or consists essentially of from 0.3 wt. % to 0.5 wt. % palladium based on the total weight of the selective hydrogenation catalyst.

The processes may include contacting the cracking C4 effluent 112 with hydrogen in the presence of the selective hydrogenation catalyst in the SHIU 130 at a temperature of from 60° C. to 80° C., a pressure of from 20 bar (2,000 kPa) to 25 bar (2,500 kPa), a weight hourly space velocity of the cracking C4 effluent 112 of 3.5 per hour, a mass flow ratio of hydrogen to diene of 2.2, or combinations of these operating conditions. The processes may include passing the hydrogenation effluent 134 directly from the SHIU 130 to the metathesis unit 140. The processes may not include removing isobutene from the cracking C4 effluent 112 or the hydrogenation effluent 134 upstream of the metathesis unit 140, thus resulting in the isobutene passing into the metathesis unit 140.

Referring again to FIG. 2, the hydrocarbon cracking unit 107 can be the high severity fluidized catalytic cracking unit 200 and the processes may include contacting the hydrocarbon feed with a cracking catalyst under high-severity conditions to produce the cracker effluent comprising at least 1-butene, 1,3-butadiene, and isobutene, where the high-severity conditions comprise a temperature of greater than or equal to 500° C., a residence time of less than 3 seconds, and a cracking catalyst to hydrocarbon weight ratio of greater than 5:1. In embodiments, the processes may include contacting the hydrocarbon feed 102 with the cracking catalyst at a temperature of from 500° C. to 800° C., for a residence time of from 0.2 seconds to 3 seconds, and at a cracking catalyst to hydrocarbon weight ratio of from 5:1 to 40:1. The hydrocarbon feed 102 may comprises crude oil, a naphtha stream, a gas condensate, or combinations of these. Referring again to FIG. 3, the hydrocarbon cracking unit 107 may comprise the steam cracking unit 300 and the processes may include contacting the hydrocarbon feed 102 with at least steam 104 in the steam cracking unit 300 at a temperature of from 700° C. to 900° C., where the contacting causes at least a portion of the hydrocarbon feed 102 to undergo steam cracking to produce cracker effluent 108.

Referring again to FIG. 1, the processes may further comprise separating the metathesis reaction effluent 146 into the metathesis C4+ effluent 158 and at least one olefin-containing effluent (metathesis ethylene effluent 154, metathesis propene effluent 156, or both), where the at least one olefin-containing effluent includes at least one of ethylene, propene, or combinations of these. The metathesis reaction effluent 146 may be separated in the metathesis effluent separation system 150, which may have any of the features or configurations previously discussed for this unit operation. The processes may further include passing the metathesis C4+ effluent 158 back to the hydrocarbon cracking unit 107. Referring again to FIG. 5, the processes may further include separating the metathesis reaction effluent 146 into at least one olefin-containing effluent, the metathesis C4 effluent 172, and the metathesis C5+ effluent 174. The processes may further include passing the metathesis C4 effluent 172 back to the SHIU 130 and passing the metathesis C5+ effluent 174 back to the hydrocarbon cracking unit 107. Referring again to FIGS. 1 and 4, the cracking catalyst may be directly downstream of the metathesis catalyst. In embodiments, the processes of the present disclosure may not include passing the metathesis ethylene effluent 154 back to the metathesis unit 140 or introducing any supplemental ethylene feed stream to the metathesis unit 140.

Referring now to FIG. 7, in some embodiments, the processes may include passing the effluent 184 from the metathesis reactor 180 to the first metathesis effluent separation unit 160 that may separate the effluent 184 from the metathesis reactor 180 into at least the metathesis ethylene effluent 154, the metathesis propene effluent 156, and the metathesis C4+ effluent 158. The processes may further include passing the metathesis C4+ effluent 158 to the cracking reactor 190 disposed downstream of the first metathesis effluent separation system 160, where the cracking reactor 190 may contact the metathesis C4+ effluent 158 with the cracking catalyst 145 to produce the cracked metathesis effluent 192. The processes may further include passing the cracked metathesis effluent 192 to the second metathesis effluent separation unit 170 downstream of the cracking reactor, where the second metathesis effluent separation unit 170 may separate the cracked metathesis effluent 192 into an olefin containing stream 178 and the metathesis C5+ effluent 174. The processes may further include passing the metathesis C5+ effluent 174 back to the hydrocarbon cracking unit 107 and passing the olefin containing stream 178 back to the first metathesis effluent separation unit 160.

The systems and processes of the present disclosure may be employed to produce olefins, such as ethylene and propene, from hydrocarbon feeds, such as naphtha and gas condensate streams. In particular, the systems and processes of the present disclosure may provide a greater selectivity towards propene compared to other commercially available processes for producing olefins through hydrocarbon cracking and metathesis. The propene produced by the systems and processes of the present disclosure may be used as intermediates in various chemical processes to produce further valuable chemical products. As a non-limiting example, the propene may be introduced to a polymerization process to make polymer materials, such as but not limited to polypropene-based polymers. Ethylene and propene may also be used as reactants in various other reactions, such as but not limited to, oxidation, alkylation, oligomerization, hydration, to produce valuable chemical products. Other known uses of the ethylene and propene produced by the systems and processes of the present disclosure are contemplated.

EXAMPLES

The following non-limiting examples illustrate one or more features of the present disclosure.

Example 1

Selective Hydrogenation/Isomerization and Metathesis of Cracking C4 Effluent Derived from Steam Cracking In Example 1, the selectivity and yield of propene from a process comprising steam cracking, selective hydrogenation and isomerization, and metathesis was determined based on operation of the SHIU 130 according to the present disclosure. For Example 1, the process was conducted using a cracking C4 effluent having a composition typically produced by steam cracking a naphtha feed. The composition of the cracking C4 effluent for Example 1 is provided in Table 2. All sulfur species such as mercaptans, $H_2S$, $CS_2$, and COS as well as heavy metals, chloride compounds and other metal impurities were removed from the cracking C4 effluent. The cracking C4 effluent was introduced to a lab scale SHIU. The lab scale SHIU included 2 reactors in series. The first reactor included a selective hydrogenation catalyst comprising 0.5 wt. % palladium supported on an alumina ($Al_2O_3$) support and was operated at a mass flow ratio of hydrogen to dienes of 1.2. The second reactor was directly downstream of the first reactor and included a selective hydrogenation catalyst comprising 0.3 wt. % palladium supported on an alumina ($Al_2O_3$) support and was operated at a mass flow ratio of hydrogen to dienes of 2.2. The amount of palladium was decreased and the mass flow ration of hydrogen to dienes was increased in the second reactor relative to the first reactor due to the decreased concentration of dienes in the effluent from the first reactor compared to the cracking C4 effluent fed to the first reactor. The SHIU (including both the first reactor and second reactor) was operated at a temperature in a range of 60° C. to 80° C., a pressure of from 20 bar to 25 bar and a weight hourly space velocity (WHSV) of 3.5 per hour. The hydrogen was 99.9% pure.

The hydrogenation effluent was passed from the SHIU to a lab scale metathesis unit comprising a metathesis catalyst and a cracking catalyst downstream of the metathesis catalyst. The metathesis catalyst included 10% tungsten oxide supported on a silica support. The cracking catalyst in the metathesis unit was a ZSM-5 type catalyst. The lab scale metathesis unit was operated at a temperature of 450° C., a pressure of from 1 bar to 3 bar, and a WHSV of the hydrogenation effluent of from 1 per hour to 5 per hour. The metathesis effluent was then passed to a separation unit that separated the metathesis effluent into an off-gas stream (light gases 152), and C2/C3 olefin stream (combination of metathesis ethylene effluent 154 and metathesis propene effluent 156), and a C4+ recycle stream (metathesis C4+ effluent 158). The compositions of the hydrogenation feed, metathesis effluent, off-gas stream, C2/C3 olefin stream, and C4+ recycle stream were analyzed according to known methods and the results are reported in Table 2.

TABLE 2

| Compound | Cracking C4 Effluent | Selective Hydrogenation (Second Reactor Effluent) | $H_2$ | Metathesis Effluent | Off-Gas | C2/C3 Stream | C4+ Recycle |
|---|---|---|---|---|---|---|---|
| Methane | — | — | — | 1.65 | 1.65 | — | — |
| Ethane | — | — | — | 0.69 | — | 0.69 | — |
| Ethylene | — | — | — | 13.20 | — | 13.20 | — |
| Propene | — | — | — | 38.52 | — | 38.52 | — |
| Propane | — | — | — | 3.67 | — | 1.47 | 2.20 |
| 1,3-Butadiene | 43.5 | 0.0 | — | 0.0 | — | — | 0.0 |
| Isobutane | 3.0 | 3.0 | — | 3.00 | — | — | 3.00 |
| n-Butane | 4.6 | 4.6 | — | 5.60 | — | — | 5.60 |
| Isobutene | 25.2 | 25.2 | — | 3.54 | — | — | 3.54 |
| 1-Butene | 15.5 | 11.7 | — | 2.34 | — | — | 2.34 |
| Cis-2-Butene | 8.2 | 55.5 | — | 6.52 | — | — | 6.52 |
| Trans-2-Butene | — | — | — | 2.27 | — | — | 2.27 |
| C5+ | — | — | — | 19.00 | — | — | 19.00 |
| Hydrogen | — | — | 3.54 | — | — | — | — |
| Total | 100.0 | 100.0 | 3.54 | 100.0 | 1.7 | 53.9 | 44.5 |

Comparative Example 2

In Comparative Example 2, a hydrogenated effluent comprising a concentration of 2-butenes less than the total combined concentration of 1-butene and isobutene was metathesized in the lab scale metathesis unit. The hydrogenation effluent of Comparative Example 2 had the nearly the same (within 0.2 wt. %) concentrations of 1,3 butadiene, isobutene, n-butane, and isobutene as the hydrogenation effluent of Example 1. For the hydrogenation effluent of Comparative Example 2, the 1-butene concentration was increase from 11.7 wt. % to 42.5 wt. % and the total concentration of 2-butenes was decreased from 55.5 wt. % to 25 wt. % relative to the hydrogenation effluent from Example 1.

The cracking C4 effluent having 2-butene <(1-butene +isobutene) was passed to the lab scale metathesis unit described in Example 1. The lab scale metathesis unit included a metathesis catalyst and a cracking catalyst downstream of the metathesis catalyst. The metathesis catalyst included 10% tungsten oxide supported on a silica support. The cracking catalyst in the metathesis unit was a ZSM-5 type catalyst. The lab scale metathesis unit was operated at the same conditions as in Example 1 (i.e., a temperature of 450° C., a pressure of from 1 bar to 3 bar, and a WHSV of the hydrogenation effluent of from 1 per hour to 5 per hour). The metathesis effluent was analyzed according to known methods without separation and the results are reported in Table 3. For comparison, Table 3 also includes the weight percentages of the constituents of the metathesis effluent from Example 1.

TABLE 3

| Compound | Hydrogenation Effluent Comp. Ex. 2 | Metathesis Effluent Comp. Ex. 2 | Metathesis Effluent of Example 1 |
|---|---|---|---|
| Methane | — | 0.42% | 1.65% |
| Ethane | — | 0.36% | 0.69% |
| Ethylene | — | 8.94% | 13.2% |
| Propene | — | 3.45% | 38.52% |
| Propane | — | 30.19% | 3.67% |
| 1,3-Butadiene | 0.0 | 1.65% | 0.0% |
| Isobutane | 3.0 | 2.75% | 3.00% |
| n-Butane | 4.5 | 3.22% | 5.60% |
| Isobutene | 25.0 | 10.02% | 3.54% |
| 1-Butene | 42.5 | 5.63% | 2.34% |
| Cis-2-Butene | 12.5 | 4.30% | 6.52% |
| Trans-2-Butene | 12.5 | 10.15% | 2.27% |
| C5+ | — | 18.92% | 19.00% |
| Total | 100.0% | 100.0% | 100.0% |

As shown in Table 3, metathesis of the stream having a concentration of 2-butenes greater than the total combined concentration of 1-butene and isobutene in the metathesis unit (Example 1) produced substantially greater yields of propene and ethylene compared to metathesis of the stream of Comparative Example 2, which had a concentration of 2-butenes less than the total combined concentration of 1-butene and isobutene. In particular, metathesizing a cracking C4 effluent having a concentration of 2-butenes greater than the combined concentration of 1-butene and isobutene, as in Example 1, produced 48% more ethylene and 1017% more propene compared to metathesizing the cracking C4 effluent of Comparative Example 2, when metathesized under the same operating conditions. Metathesis of the cracking C4 effluent of Comparative Example 2 further resulted in a greater yield of propane, an order of magnitude greater, compared to Example 1, when metathesized under the same operating conditions. Propane is substantially less valuable compared to propene. Thus, operating the SHIU to produce a hydrogenation effluent having a concentration of 2-butenes greater than the total combined concentration of 1-butene and isobutene can result in unexpectedly greater yields of propene and ethylene when the hydrogenation effluent is metathesized in the metathesis unit of the present disclosure.

Example 3

Selective Hydrogenation/Isomerization and Metathesis of Cracking C4 Effluent Derived from High-Severity Fluidized Catalytic Cracking In Example 3, the selectivity and yield of propene from a process comprising high-severity fluidized catalytic cracking, selective hydrogenation and isomerization, and metathesis was determined based on operation of the SHIU 130 according to the present disclosure. For Example 3, the process was conducted using a cracking C4 effluent having a composition typically produced by high-severity fluidized catalytic cracking of an AXL crude oil feed. The composition of the cracking C4 effluent for Example 3 is provided in Table 4. All sulfur species such as mercaptans, $H_2S$, $CS_2$, and COS as well as heavy metals, chloride compounds and other metal impurities were removed from the cracking C4 effluent. The cracking C4 effluent was introduced to the lab scale SHIU previously described in Example 1. The SHIU was operated at the same operating conditions described in Example 1. The hydrogenation effluent was passed from the SHIU to the lab scale metathesis unit having the same catalysts and same operating conditions described in Example 1. The metathesis effluent was then passed to a separation unit that separated the metathesis effluent into an off-gas stream (light gases 152), and C2/C3 olefin stream (combination of metathesis ethylene effluent 154 and metathesis propene effluent 156), and a C4+ recycle stream (metathesis C4+ effluent 158). The compositions of the hydrogenation feed, metathesis effluent, off-gas stream, C2/C3 olefin stream, and C4+ recycle stream for Example 3 were analyzed according to known methods and the results are reported in Table 4.

TABLE 4

| Compound | Cracking C4 Effluent | Hydrogenation Effluent | $H_2$ | Metathesis Effluent | Off-Gas | C2/C3 Stream | C4+ Recycle |
|---|---|---|---|---|---|---|---|
| Methane | — | — | — | 1.46 | 1.46 | — | — |
| Ethane | — | — | — | 0.61 | — | 0.61 | — |
| Ethylene | — | — | — | 11.69 | — | 11.69 | — |
| Propene | — | — | — | 34.11 | — | 34.11 | — |

TABLE 4-continued

| Compound | Cracking C4 Effluent | Hydrogenation Effluent | H$_2$ | Metathesis Effluent | Off-Gas | C2/C3 Stream | C4+ Recycle |
|---|---|---|---|---|---|---|---|
| Propane | — | — | — | 3.25 | — | 1.30 | 1.95 |
| 1,3-Butadiene | 1.2 | 0.0 | — | 0.0 | — | — | 0.0 |
| Isobutane | 11.0 | 11.0 | — | 11.00 | — | — | 11.00 |
| n-Butane | 7.3 | 7.3 | — | 8.19 | — | — | 8.19 |
| Isobutene | 24.2 | 24.2 | — | 3.40 | — | — | 3.40 |
| 1-Butene | 16.1 | 8.6 | — | 1.73 | — | — | 1.73 |
| Cis-2-Butene | 40.2 | 48.9 | — | 5.74 | — | — | 5.74 |
| Trans-2-Butene | | | — | 2.00 | — | — | 2.00 |
| C5+ | — | — | — | 16.83 | — | — | 16.83 |
| Hydrogen | — | — | 0.10 | — | — | — | — |
| Total | 100.0 | 100.0 | 0.10 | 100.0 | 1.5 | 47.7 | 50.8 |

As shown in Table 4, metathesizing the hydrogenation effluent produced from the cracking C4 effluent from fluidized catalytic cracking can produce 12% ethylene and 34% propene when the SHIU is operated to produce a hydrogenation effluent having a concentration of 2-butenes that is greater than the total combined concentrations of 1-butene and isobutene.

A first aspect of the present disclosure is directed to a process for producing olefins. The process may include passing a hydrocarbon feed to a hydrocarbon cracking unit that cracks at least a portion of the hydrocarbon feed to produce a cracker effluent and passing the cracker effluent to a cracker effluent separation system that separates the cracker effluent to produce at least a cracking C4 effluent. The cracking C4 effluent may comprise at least 1-butene, 1,3-butadiene, and isobutene. The process may further comprise passing the cracking C4 effluent to a selective hydrogenation and isomerization unit that contacts the cracking C4 effluent with hydrogen in the presence of a selective hydrogenation catalyst to produce a hydrogenation effluent. Contacting the cracking C4 effluent with the hydrogen in the presence of the selective hydrogenation catalyst may hydrogenate 1,3-butadiene to 1-butene, n-butane, or both and isomerizes at least a portion of the 1-butene to 2-butenes. A concentration of 2-butenes in the hydrogenation effluent may be greater than or equal to a sum of a concentration of 1-butene and a concentration of isobutene in the hydrogenation effluent. The process may further comprise passing the hydrogenation effluent to a metathesis unit that contacts the hydrogenation effluent with a metathesis catalyst and a cracking catalyst downstream of the metathesis catalyst to produce a metathesis reaction effluent comprising at least propene. The contacting with the metathesis catalyst may cause metathesis of at least a portion of the 1-butene, 2-butenes, and isobutene in the hydrogenation effluent to produce a metathesis reaction product, and the contacting with the cracking catalyst may cause at least a portion of C5+ olefins produced through metathesis to undergo cracking reactions to produce propene, ethylene, or both.

A second aspect of the present disclosure may include the first aspect, where the concentration of 2-butenes in the hydrogenation effluent greater than or equal to the sum of the concentration of 1-butene and the concentration of isobutene in the hydrogenation effluent may promote formation of propene and suppresses formation of ethylene in the metathesis unit.

A third aspect of the present disclosure may include either one of the first or second aspects, where a concentration of isobutene in the hydrogenation effluent may be from 15 wt. % to 50 wt. % per unit weight of the hydrogenation effluent.

A fourth aspect of the present disclosure may include any one of the first through third aspects, where the hydrogenation effluent may have a mass ratio of 2-butenes to a sum of isobutene and 1-butene of from 1:1 to 9:1, from 1:1 to 4:1, from 1:1 to 3:1, or from 1:1 to 2:1.

A fifth aspect of the present disclosure may include any one of the first through fourth aspects, where the selective hydrogenation catalyst may comprise a transition metal supported on an alumina catalyst support.

A sixth aspect of the present disclosure may include the fifth aspect, where the transition metal may comprise palladium.

A seventh aspect of the present disclosure may include the sixth aspect, an amount of palladium may be from 0.01 weight percent to 1 weight percent based on the total weight of the selective hydrogenation catalyst.

An eighth aspect of the present disclosure may include any one of the first through seventh aspects, comprising contacting the cracking C4 effluent with hydrogen in the presence of the selective hydrogenation catalyst at a temperature of from 60 degrees Celsius to 80 degrees Celsius, a pressure of from 20 bar (2,000 kilopascals) to 25 bar (2,500 kilopascals), a weight hourly space velocity of the cracking C4 effluent of from 2 per hour to 4 per hour, a mass flow ratio of hydrogen to diene of from 0.1 to 3, or combinations of these conditions, where the mass flow ratio of hydrogen to diene may be a mass flow rate of hydrogen to the hydrogenation and isomerization unit divided by a product of a weight fraction of dienes in the cracking C4 effluent and a mass flow rate of the cracking C4 effluent to the hydrogenation and isomerization unit.

A ninth aspect of the present disclosure may include any one of the first through eighth aspects, comprising passing the hydrogenation effluent directly from the selective hydrogenation and isomerization unit to the metathesis unit.

A tenth aspect of the present disclosure may include any one of the first through ninth aspects, where the isobutene is not removed from the cracking C4 effluent or the hydrogenation effluent upstream of the metathesis unit.

An eleventh aspect of the present disclosure may include any one of the first through tenth aspects, where the hydrocarbon cracking unit may comprise a high severity fluidized catalytic cracking unit and the process may comprises contacting the hydrocarbon feed with a cracking catalyst under high-severity conditions to produce the cracker effluent comprising at least 1-butene, 1,3-butadiene, and isobutene, where the high-severity conditions may comprise a temperature of greater than or equal to 500° C., a residence time of less than 3 seconds, and a cracking catalyst to hydrocarbon weight ratio of greater than 5:1.

A twelfth aspect of the present disclosure may include the eleventh aspect, comprising contacting the hydrocarbon feed with the cracking catalyst at a temperature of from 500° C. to 800° C., for a residence time of from 0.2 seconds to 3 seconds, and at a cracking catalyst to hydrocarbon weight ratio of from 5:1 to 40:1.

A thirteenth aspect of the present disclosure may include any one of the first through tenth aspects, where the hydrocarbon cracking unit may comprise a steam cracking unit and the process may comprise contacting the hydrocarbon feed with at least steam at a temperature of from 700 degrees Celsius (° C.) to 900° C., where the contacting may cause at least a portion of the hydrocarbon feed to undergo steam cracking to produce the cracker effluent.

A fourteenth aspect of the present disclosure may include any one of the first through thirteenth aspects, further comprising separating the metathesis reaction effluent into a metathesis C4+ effluent and at least one olefin-containing effluent, the at least one olefin-containing effluent comprising at least one of ethylene, propene, or combinations of these.

A fifteenth aspect of the present disclosure may include the fourteenth aspect, further comprising passing the metathesis C4+ effluent back to the hydrocarbon cracking unit.

A sixteenth aspect of the present disclosure may include any one of the first through fifteenth aspects, further comprising separating the metathesis reaction effluent into at least one olefin-containing effluent, a metathesis C4 effluent, and a metathesis C5+ effluent.

A seventeenth aspect of the present disclosure may include the sixteenth aspect, further comprising passing the metathesis C4 effluent to the selective hydrogenation and isomerization unit and passing the metathesis C5+ effluent to the hydrocarbon cracking unit.

An eighteenth aspect of the present disclosure may include any one of the first through seventeenth aspects, where the cracking catalyst may be directly downstream of the metathesis catalyst.

A nineteenth aspect of the present disclosure may include any one of the first through eighteenth aspects, where a metathesis ethylene effluent is not passed back into contact with the metathesis catalyst and no supplemental ethylene is introduced into contact with the metathesis catalyst.

A twentieth aspect of the present disclosure may include any one of the first through nineteenth aspects, where the metathesis unit may comprise a metathesis reactor comprising the metathesis catalyst and a cracking reactor comprising the cracking catalyst, where the cracking reactor may be separate from and downstream from the metathesis reactor.

A twenty-first aspect of the present disclosure may include the twentieth aspect, comprising passing a metathesis reactor effluent from the metathesis reactor to a first metathesis effluent separation unit that separates the metathesis reactor effluent into at least a metathesis ethylene effluent, a metathesis propene effluent, and a metathesis C4+ effluent; passing the metathesis C4+ effluent to the cracking reactor disposed downstream of the first metathesis effluent separation system, where the cracking reactor may contact the metathesis reactor effluent with the cracking catalyst to produce a cracked metathesis effluent; passing the cracked metathesis effluent to a second metathesis effluent separation unit downstream of the cracking reactor, where the second metathesis effluent separation unit may separate the cracked metathesis effluent into an olefin containing stream and a metathesis C5+ effluent; passing the metathesis C5+ effluent to the hydrocarbon cracking unit; and passing the olefin containing stream to the first metathesis effluent separation unit.

A twenty-second aspect of the present disclosure may include any one of the first through twenty-first aspects, where the cracker effluent separation system may comprise one or a plurality of separators that separate the cracker effluent into the cracking C4 effluent and at least one of a cracking propene effluent, a cracking ethylene effluent, a light gas effluent, a greater boiling effluent, or combinations of these.

A twenty-third aspect of the present disclosure is directed to a system for producing olefins. The system may comprise a hydrocarbon feed; a hydrocarbon cracking system in fluid communication with the hydrocarbon feed, the hydrocarbon cracking system comprising a hydrocarbon cracking unit and a cracker effluent separation system downstream of the hydrocarbon cracking unit; a selective hydrogenation and isomerization unit downstream of the cracker effluent separation system, the selective hydrogenation and isomerization unit comprising a selective hydrogenation catalyst; a metathesis unit downstream of the selective hydrogenation and isomerization unit, the metathesis unit comprising a metathesis catalyst disposed in a metathesis reaction zone and a cracking catalyst disposed in a cracking reaction zone downstream of the metathesis reaction zone; and a control system communicatively coupled to the hydrocarbon cracking unit, the cracker effluent separation system, the selective hydrogenation and isomerization unit, and the metathesis unit. The control system may comprise at least one processor, at least one memory module communicatively coupled to the at least one processor, and machine readable and executable instructions stored on the at least one memory module. The machine readable and executable instructions, when executed by the at least one processor, may cause the control system to automatically: operate the hydrocarbon cracking unit to thermally or catalytically crack at least a portion of a hydrocarbon feed to produce a cracker effluent comprising olefins; operate the cracker effluent separation system to separate the cracker effluent to produce at least a cracking C4 effluent comprising at least 1-butene, isobutene, and 1,3-butadiene; operate the selective hydrogenation and isomerization unit to contact the cracking C4 effluent with hydrogen in the presence of the selective hydrogenation catalyst to produce a hydrogenation effluent; maintain the selective hydrogenation and isomerization unit under operating conditions sufficient to convert the 1,3-butadiene to 1-butene and isomerize 1-butene to 2-butene so that a concentration of 2-butenes in the hydrogenation effluent is greater than or equal to a sum of a concentration of 1-butene and a concentration of isobutene in the hydrogenation effluent; and operate the metathesis system to contact the hydrogenation effluent with the metathesis catalyst and cracking catalyst to produce a metathesis reaction effluent comprising at least propene.

A twenty-fourth aspect of the present disclosure may include the twenty-third aspect, where the selective hydrogenation catalyst may comprise from 0.01 weight percent to 1 weight percent transition metal supported on an alumina catalyst support.

A twenty-fifth aspect of the present disclosure may include either one of the twenty-third or twenty-fourth aspects, where the machine readable and executable instructions, when executed by the at least one processor, may cause the control system to automatically operate the selective hydrogenation and isomerization unit at one or a plurality of the following operating conditions: a temperature of from 60 degrees Celsius to 80 degrees Celsius; a pressure of from 20 bar (2,000 kilopascals) to 25 bar (2,500 kilopascals); a weight hourly space velocity of the cracking C4 effluent of from 2 per hour to 4 per hour, or about 3.5 per hour; a mass flow ratio of hydrogen to diene of from 0.1 to 3, or about 2.2, where the mass flow ratio of hydrogen to diene is a mass flow rate of hydrogen to the hydrogenation and isomerization unit divided by a product of a weight fraction of dienes in the cracking C4 effluent and a mass flow rate of the cracking C4 effluent to the hydrogenation and isomerization unit; or combinations of these.

A twenty-sixth aspect of the present disclosure may include any one of the twenty-third through twenty-fifth aspects, where the hydrocarbon cracking unit may be a high-severity fluidized catalytic cracking unit and the machine readable and executable instructions, when executed by the at least one processor, may cause the control system to automatically operate the high-severity fluidized catalytic cracking unit to contact the hydrocarbon feed with a cracking catalyst under high-severity conditions, where the high-severity conditions may comprise a temperature of greater than or equal to 500° C., a residence time of less than 3 seconds, a cracking catalyst to hydrocarbon weight ratio of greater than 5:1, or combinations of these conditions.

A twenty-seventh aspect of the present disclosure may include any one of the twenty-third through twenty-fifth aspects, where the hydrocarbon cracking unit may be a steam cracking unit and the machine readable and executable instructions, when executed by the at least one processor, may cause the control system to automatically operate the steam cracking unit to contact the hydrocarbon feed with steam at a temperature of from 700° C. to 900° C.

A twenty-eighth aspect of the present disclosure may include any one of the twenty-third through twenty-seventh aspects, further comprising a metathesis effluent separation system disposed downstream of the metathesis unit and communicatively coupled to the control system.

A twenty-ninth aspect of the present disclosure may include the twenty-eighth aspect, where the machine readable and executable instructions, when executed by the at least one processor, may cause the control system to automatically operate the metathesis effluent separation system to separate the metathesis reaction effluent into at least a metathesis propene effluent and a metathesis C4+ effluent; and pass at least a portion of the metathesis C4+ effluent back to the hydrocarbon cracking unit.

A thirtieth aspect of the present disclosure may include the twenty-ninth aspect, where the machine readable and executable instructions, when executed by the at least one processor, may cause the control system to automatically operate the metathesis effluent separation system to further separate the metathesis C4+ effluent into a metathesis C4 effluent and a metathesis C5+ effluent; pass at least a portion of the metathesis C5+ effluent to the hydrocarbon cracking unit; and pass at least a portion of the metathesis C4 effluent to the selective hydrogenation and isomerization unit.

A thirty-first aspect of the present disclosure may include any one of the twenty-third through thirtieth aspects, where the metathesis system may be in direct fluid communication with the selective hydrogenation and isomerization unit so that the hydrogenation effluent passes directly from the selective hydrogenation and isomerization unit to the metathesis system.

A thirty-second aspect of the present disclosure may include any one of the twenty-third through thirty-first aspects, where the metathesis catalyst and the cracking catalyst may be disposed in a single reactor so that the hydrogenation effluent passed to the metathesis system contacts the metathesis catalyst and then the cracking catalyst directly after contacting the metathesis catalyst.

A thirty-third aspect of the present disclosure may include any one of the twenty-third through thirty-first aspects, where the metathesis catalyst may be disposed in a metathesis reactor and the cracking catalyst may be disposed in a cracking reactor separate from the metathesis reactor.

A thirty-fourth aspect of the present disclosure may include the thirty-third aspect, where the cracking reactor may be directly downstream of the metathesis reactor and a conduit may extend directly between the metathesis reactor and the cracking reactor so that a metathesis reactor effluent can be passed directly from the metathesis reactor to the cracking reactor.

A thirty-fifth aspect of the present disclosure may include any one of the twenty-third through thirty-fourth aspects, where the system does not include a supplemental ethylene feed to the metathesis unit.

It should now be understood that various aspects of the systems and processes for producing olefins that include high-severity fluidized catalytic cracking integrated with metathesis are described and such aspects may be utilized in conjunction with various other aspects.

Throughout this disclosure ranges are provided for various processing parameters and operating conditions for the systems and processes for producing olefins and the compositions of various streams and mixtures. It will be appreciated that when one or more explicit ranges are provided the individual values and the sub-ranges formed within the range are also intended to be provided as providing an explicit listing of all possible combinations is prohibitive. For example, a provided range of 1-10 also includes the individual values, such as 1, 2, 3, 4.2, and 6.8, as well as all the ranges that may be formed within the provided bounds, such as 1-8, 2-4, 6-9, and 1.3-5.6.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. A process for producing olefins, the process comprising:
   passing a hydrocarbon feed to a hydrocarbon cracking unit that cracks at least a portion of the hydrocarbon feed to produce a cracker effluent;
   passing the cracker effluent to a cracker effluent separation system that separates the cracker effluent to produce at least a cracking C4 effluent, where the cracking C4 effluent comprises at least 1-butene, 1,3-butadiene, and isobutene;
   passing the cracking C4 effluent to a selective hydrogenation and isomerization unit that contacts the cracking C4 effluent with hydrogen in the presence of a selective hydrogenation catalyst at a temperature of from 60 degrees Celsius to 80 degrees Celsius and a pressure of from 20 bar (2,000 kilopascals) to 25 bar (2,500 kilopascals) to produce a hydrogenation effluent, where:
  contacting the cracking C4 effluent with the hydrogen in the presence of the selective hydrogenation catalyst hydrogenates 1,3-butadiene to 1-butene, n-butane, or both and isomerizes at least a portion of the 1-butene to 2-butenes; and
  passing the hydrogenation effluent to a metathesis unit that contacts the hydrogenation effluent with a metathesis catalyst and a cracking catalyst downstream of the metathesis catalyst to produce a metathesis reaction effluent comprising at least propene, where:
    a concentration of 2-butenes in the hydrogenation effluent passed to the metathesis unit is greater than or equal to a sum of a concentration of 1-butene and a concentration of isobutene in the hydrogenation effluent;
    the concentration of isobutene in the hydrogenation effluent passed to the metathesis unit is greater than or equal to 18 wt. %;
    contacting with the metathesis catalyst causes metathesis of at least a portion of the 1-butene, 2-butenes, and isobutene in the hydrogenation effluent to produce a metathesis reaction product; and
    contacting with the cracking catalyst causes at least a portion of C5+ olefins produced through metathesis to undergo cracking reactions to produce propene, ethylene, or both.

2. The process of claim 1, where the concentration of 2-butenes in the hydrogenation effluent greater than or equal to the sum of the concentration of 1-butene and the concentration of isobutene in the hydrogenation effluent promotes formation of propene and suppresses formation of ethylene in the metathesis unit.

3. The process of claim 1, where a concentration of isobutene in the hydrogenation effluent passed to the metathesis unit is from 18 wt. % to 50 wt. % per unit weight of the hydrogenation effluent.

4. The process of claim 1, where the hydrogenation effluent has a mass ratio of 2-butenes to a sum of isobutene and 1-butene of from 1:1 to 9:1.

5. The process of claim 1, where the selective hydrogenation catalyst comprises a transition metal supported on an alumina catalyst support.

6. The process of claim 5, where the transition metal comprises palladium in an amount of from 0.01 weight percent to 1 weight percent based on the total weight of the selective hydrogenation catalyst.

7. The process of claim 1, where the contacting the cracking C4 effluent with hydrogen in the presence of the selective hydrogenation catalyst further comprises contacting the cracking C4 effluent with the hydrogen in the presence of the selective hydrogenation catalyst at a weight hourly space velocity of the cracking C4 effluent of from 2 per hour to 4 per hour, a mass flow ratio of hydrogen to diene of from 0.1 to 3, or both of these conditions, where the mass flow ratio of hydrogen to diene is a mass flow rate of hydrogen to the hydrogenation and isomerization unit divided by a product of a weight fraction of dienes in the cracking C4 effluent and a mass flow rate of the cracking C4 effluent to the hydrogenation and isomerization unit.

8. The process of claim 1, comprising passing the hydrogenation effluent directly from the selective hydrogenation and isomerization unit to the metathesis unit.

9. The process of claim 1, where the hydrocarbon cracking unit comprises a high severity fluidized catalytic cracking unit and the process comprises contacting the hydrocarbon feed with a cracking catalyst under high-severity conditions to produce the cracker effluent comprising at least 1-butene, 1,3-butadiene, and isobutene, where the high-severity conditions comprise a temperature of greater than or equal to 500° C., a residence time of less than 3 seconds, and a cracking catalyst to hydrocarbon weight ratio of greater than 5:1.

10. The process of claim 1, where the hydrocarbon cracking unit comprises a steam cracking unit and the process comprises contacting the hydrocarbon feed with at least steam at a temperature of from 700 degrees Celsius (° C.) to 900° C., where contacting causes at least a portion of the hydrocarbon feed to undergo steam cracking to produce the cracker effluent.

11. The process of claim 1, further comprising separating the metathesis reaction effluent into a metathesis C4+ effluent and at least one olefin-containing effluent, the at least one olefin-containing effluent comprising at least one of ethylene, propene, or combinations of these and passing the metathesis C4+ effluent back to the hydrocarbon cracking unit.

12. The process of claim 1, further comprising:
  separating the metathesis reaction effluent into at least one olefin-containing effluent, a metathesis C4 effluent, and a metathesis C5+ effluent;
  passing the metathesis C4 effluent to the selective hydrogenation and isomerization unit; and
  passing the metathesis C5+ effluent to the hydrocarbon cracking unit.

13. The process of claim 1, where:
the metathesis unit comprises a metathesis reactor comprising the metathesis catalyst and a cracking reactor comprising the cracking catalyst;
the cracking reactor is separate from and downstream from the metathesis reactor; and
the process further comprises:
  passing a metathesis reactor effluent from the metathesis reactor to a first metathesis effluent separation unit that separates the metathesis reactor effluent into at least a metathesis ethylene effluent, a metathesis propene effluent, and a metathesis C4+ effluent;
  passing the metathesis C4+ effluent to the cracking reactor disposed downstream of the first metathesis effluent separation system, where the cracking reactor contacts the metathesis reactor effluent with the cracking catalyst to produce a cracked metathesis effluent;
  passing the cracked metathesis effluent to a second metathesis effluent separation unit downstream of the cracking reactor, where the second metathesis effluent separation unit separates the cracked metathesis effluent into an olefin containing stream and a metathesis C5+ effluent;
  passing the metathesis C5+ effluent to the hydrocarbon cracking unit; and
  passing the olefin containing stream to the first metathesis effluent separation unit.

14. The process of claim 1, where the selective hydrogenation and isomerization unit comprises one or a plurality of fixed bed reactors.

15. The process of claim 1, wherein the concentration of isobutene in the hydrogenation effluent passed to the metathesis unit is less than or equal to 30 wt. %.

16. The process of claim 1, wherein the concentration of 1-butene in the hydrogenation effluent passed to the metathesis unit is greater than or equal to 10 wt. % and less than or equal to 30 wt. %.

* * * * *